(12) United States Patent
Ding et al.

(10) Patent No.: US 7,112,429 B2
(45) Date of Patent: Sep. 26, 2006

(54) THERMAL TOLERANT MANNANASE FROM ACIDOTHERMUS CELLULOLYTICUS

(75) Inventors: Shi-You Ding, Golden, CO (US); William S. Adney, Golden, CO (US); Todd B. Vinzant, Golden, CO (US); Michael E. Himmel, Littleton, CO (US)

(73) Assignee: Midwest Research Institute, Kansas City, MO (US)

( * ) Notice: Subject to any disclaimer, the term of this patent is extended or adjusted under 35 U.S.C. 154(b) by 0 days.

(21) Appl. No.: 09/917,378

(22) Filed: Jul. 28, 2001

(65) Prior Publication Data

US 2003/0119093 A1   Jun. 26, 2003

(51) Int. Cl.
*C12N 9/00* (2006.01)
*C12N 9/44* (2006.01)
*C11D 3/00* (2006.01)
*C11D 7/42* (2006.01)
*C07H 21/04* (2006.01)
*C12P 21/06* (2006.01)

(52) U.S. Cl. .............................. 435/210; 435/4; 435/6; 435/69.1; 435/183; 435/200; 435/252.3; 435/320.1; 536/23.2; 536/23.7; 510/114; 510/392; 510/515

(58) Field of Classification Search ........ 435/183–210, 435/41, 99, 100, 104, 105, 277, 4, 6, 69.1, 435/252.3, 320.1, 262, 274, 263; 530/350; 536/23.2–23.74; 510/114, 392, 515
See application file for complete search history.

(56) References Cited

U.S. PATENT DOCUMENTS

| 5,110,735 | A |   | 5/1992  | Tucker et al.     |
| 5,366,884 | A |   | 11/1994 | Adney et al.      |
| 5,432,075 | A |   | 7/1995  | Himmel et al.     |
| 5,514,584 | A |   | 5/1996  | Lastick et al.    |
| 5,536,655 | A |   | 7/1996  | Thomas et al.     |
| 5,712,142 | A |   | 1/1998  | Adney et al.      |
| 6,013,860 | A |   | 1/2000  | Himmel et al.     |
| 6,060,299 | A |   | 5/2000  | Sreckrishna et al.|
| 6,126,698 | A | * | 10/2000 | Liu et al.        |

OTHER PUBLICATIONS

Himmel et al. Genseq database Accession No. AAR89927, Oct. 8, 1996.*

Himmel et al. Genseq database Accession No. AAB48786, Nov. 23, 2000.*

Himmel et al. (Genseq database Accession No AAB 48787, Nov. 23, 2000.*

Gibbs et al. Appl. Environ. Microbiol., 1992, vol. 58(12):3864-3867.*

Johnson et al. (World J. Microbiol. Biotechnol., 1990, vol. 6(3):245-254).*

1993, Al-Sulami, A. A., et al., "Purification and Properties of Cellulases from a Local Isolate of *Cellulomonas flavigena.*" *Dirasat*, vol. 19B, No. 4 (1992), pp. 139-155 (Univ.Jordan).

1995, Baker, J. O., et al. "Synergism Between Purified Bacterial and Fungal Cellulases." *Enzymatic Degredation of Insoluble Carbohydrates*, Am. Chem. Society Symp. Ser. vol. 618 (1995) pp. 113-141.

A. Sunna, et al., "A Gene Encoding a Novel Multidomain Beta-1, 4-Mannanase from Caldibacillus cellulovorans and Action of the Recombinant Enzyme on Kraft Pulp," Applied and Environmental Microbiology, vol. 66, No. 2, Feb. 2000, pp. 664-670, XP002192691.

Seikagaku Kogyo Co Ltd., "New Endo-Beta-Mannosidases isolated from Liliaceae Plants-Useful for Analysis of Sugar Chain Structure," Derwent Publication Ltd., Sec. Ch, Week 200022, London, GB, Blass B04 AN 2000-249670, XP002192693.

Tucker, M. et al., "Ultra-Thermostable Cellulases from Acidothermus: Comparison of Temperature Optima with Previously Reported Cellulases, " Bio/Technology, vol. 7, Aug. 1989, pp. 817-820.

Thomas, S. et al., "Gene Coding for the E1 Endoglucanase," PCT International Patent Application No. PCT/US95/08868, Feb. 1, 1996, WO 96/2551A1.

Bylina, E.J. et al., "Glycosidase Enzymes," PCT International Patent Application No. PCT/US97/00092, Jul. 17, 1997, WO 97/25417.

* cited by examiner

*Primary Examiner*—Manjunath N. Rao
(74) *Attorney, Agent, or Firm*—Paul J. White

(57) ABSTRACT

The invention provides a thermal tolerant mannanase that is a member of the glycoside hydrolase family. The invention further discloses this mannanase as ManA. ManA has been isolated and characterized from *Acidothermus cellulolyticus*. The invention further provides recombinant forms of the identified ManA. Methods of making ManA polypeptides, including fusions, variants, and derivatives, are also disclosed. Methods of using mannanase A, including for the processing of food and for use in food stuffs as bulking agents and the like, are also disclosed.

6 Claims, 2 Drawing Sheets

THERMAL TOLERANT MANNANASE FROM ACIDOTHERMUS CELLULOLYTICUS

STATEMENT AS TO FEDERALLY SPONSORED RESEARCH

The United States Government has rights in this invention under Contract No. DE-AC36-99GO10337 between the United States Department of Energy and the National Renewable Energy Laboratory, a Division of the Midwest Research Institute.

FIELD OF THE INVENTION

The invention generally relates to a novel mannanase from *Acidothermus cellulolyticus*, ManA. More specifically, the invention relates to purified and isolated ManA polypeptides, nucleic acid molecules encoding the polypeptides, and processes for production and use of ManA, as well as variants and derivatives thereof.

BACKGROUND OF THE INVENTION

Plant biomass is the most abundant source of carbohydrate in the world due to the lignocellulosic materials comprising the cell walls of all higher plants. Plant cell walls are divided into primary and secondary cell walls. The primary cell wall, which provides structure for expanding cells (and hence changes as the cell grows), is composed of three major polysaccharides, cellulose, hemicellulose and pectin, and one group of glycoproteins. The secondary cell wall, which is produced after the cell has completed growing, also contains polysaccharides and is strengthened through polymeric lignin covalently cross-linked to hemicellulose.

Hemicellulose is a general term used to refer to cell wall polysaccharides that are not celluloses or pectins. Hemicellulose sugar backbones include a variety of compounds, including xylans, xyloglucans, arabinoxylans and mannans. One of the chief constituents of hemicellulose is the aldohexose glucose, mannose, which also may be in the form of a pyranose ring structure, β-D-mannose. With respect to mannose, the glycosidic linkage is on the 1-carbon as a β-bond, having available linkage sites at the 2-, 3-, 4-, and 6-carbons.

A particularly rich source of mannans is the hemicellulose content of softwood, and in particular, the waste material from softwood processing in paper manufacturing. One of the more important hemicelluloses in softwood is galactoglucomannan, which is composed of a backbone of β-(1,4)-linked D-mannopyranose and D-glucopyranose in a ratio of approximately 3:1, respectively (Sjostrom, E. (1992) Wood Chemistry, 2nd Ed., Academic Press: New York, N.Y., pp 63–70). Other sources of mannans include the endosperm of copra and ivory palm nuts, guar beans, coffee beans, and roots of konjak (*Amorphophallus konjac*).

Enzymatic degradation of the β-linkages in β-1,4-D-mannans requires the coordinate action of several mannanases. Mannanases have been identified in *Bacillus* (Emi et al., (1972) *Agr. Biol. Chem.* 36:991–1001), *Aeromonas* (Araki et al., (1983) *Agr. Kyushu Univ.* 27:89–98), *Streptomyces* (Takahashi et al., (1984) *Biol. Chem.* 48:2189–2195) and several fungal species (Hashimoto et al., (1969) *J. Nippon Nogeikagaku Kaishi* 43:317–322).

Mannanases are given an Enzyme Commission (EC) designation according to the Nomenclature Committee of the International Union of Biochemistry and Molecular Biology (Eur. J. Biochem. 264:607–609 and 610–650 (1999)). β-mannosidase (EC 3.2.1.25) (Hylin et al., (1964) *J. Biol. Chem.*, 239:990) and β-mannanase (EC 3.2.1.78) (Reese, E. T., (1965) *Can. J. Microbiol.* 11:167) cleave the β-mannoside linkages in β-1,4-D-mannans to yield D-mannose and manno-oligosaccharides, respectively. Other mannanase activities have been identified, for example, exomannanase (1,4-β-D-Mannan mannohydrolase) (EC 3.2.1.xx—unassigned) and exomannobiohydrolase (1,4-β-D-Mannan mannobiohydrolase) (EC 3.2.1.100) (McCleary, B. V., (1988) *Methods Enzymol.* 160:589–595; Araki et al., (1982) *J. Biochem.* 91:1181).

Industrial applications of hemicellulases, and mannanases in particular, are primarily targeted at situations where selective removal of hemicellulose is required to elevate the value of a complex substrate, such as in foods, feeds, and paper pulp. Food industry applications include the processing of coffee (Godfrey, T, (1983) in *Industrial Enxymology: The Applications of Enzymes in Industry*, Godfrey and Reichelt, eds., MacMillan Press: Basingstoke, UK, pp 340–351) the maceration of fruits and vegetables (Biely, P, (1985) *Trends Biotechnol.* 3:286–290), and bread preparation (Maat et al., (1992) *Xylans and Xylanases*, Visser, J., Beldman M., Kusters-van Someren and Voragen, eds., Elsevier: New York, N.Y., pp 349–360). Feed industry applications includes the processing of poultry feed (van Paridon et al., (1992) *Xylans and Xylanases*, Visser, J., Beldman M., Kusters-van Someren and Voragen, eds., Elsevier: New York, N.Y., pp 371–378).

In addition, mannanases can be useful in the production of biofuels from plant biomass, where the mannanases participate in the hydrolysis of the hemicellulose fraction to simpler sugars, which are then converted to ethanol via fermentation.

Highly thermostable enzymes have been isolated from the thermophile *Acidothermus cellulolyticus* gen. nov., sp. nov., a bacterium originally isolated from decaying wood in an acidic, thermal pool at Yellowstone National Park (Mohagheghi et al., (1986) *Int. J. Systematic Bacteriology* 36(3): 435–443). One cellulase enzyme produced by this organism, the endoglucanase EI, is known to display maximal activity at 75° C. to 83° C. (Tucker et al., *Bio/Technology*, 7(8): 817–820). E1 endoglucanase has been described in U.S. Pat. No. 5,275,944. The *A. cellulolyticus* E1 endoglucanase is an active cellulase; in combination with exocellulase CBH I from *Trichoderma reesei*, E1 gives high levels of saccharification and contributes to a degree of synergism. Baker et al., (1994) *Appl. Biochem. Biotechnol.* 45/46:245–256. The gene encoding E1 catalytic and cellulose binding domains and linker peptide were described in U.S. Pat. No. 5,536, 655. The potential exists for the successful, commercial scale expression of heterologous mannanases, and in particular thermal stable mannanases. Like the E1 endoglucanase, thermal stable mannanases would likely have the desirable characteristic of maximal activity at elevated temperatures, as well as potentially having the thermal tolerant associated properties of resistance to acid inactivation, proteolytic inactivation, and solvent inactivation (Cowan D A in Danson M J et al. (1992) The *Archaebacteria, Biochemistry and Biotechnology* at 149–159, University Press, Cambridge, ISBN 1855780100). E1 has also been expressed as a stable, active enzyme from a wide variety of hosts, including *E. coli, Streptomyces lividans, Pichia pastoris*, cotton, tobacco, and Arabidopsis (Dai Z, Hooker B S, Anderson D B, Thomas S R. *Transgenic Res.* 2000 February; 9(1):43–54).

There is a need within the art to generate alternative mannanase enzymes capable of assisting in the commercial scale processing of mannans to simpler sugars for use in the food, feed, paper pulp and biofuels industries. Against this backdrop the present invention has been developed.

SUMMARY OF THE INVENTION

The present invention provides ManA, a novel member of the glycoside hydrolase (GH) family of enzymes, and in particular a thermal tolerant glycoside hydrolase useful in the degradation of mannans. ManA polypeptides of the invention include those having an amino acid sequence shown in SEQ ID NO:1, as well as polypeptides having substantial amino acid sequence identity to the amino acid sequence of SEQ ID NO:1 and useful fragments thereof, including, a catalytic domain having significant sequence similarity to the GH5 family, a first carbohydrate binding domain (type II) and a second carbohydrate binding domain (type III).

The invention also provides a polynucleotide molecule encoding ManA polypeptides and fragments of ManA polypeptides, for example catalytic and carbohydrate binding domains. Polynucleotide molecules of the invention include those molecules having a nucleic acid sequence as shown in SEQ ID NO:2; those that hybridize to the nucleic acid sequence of SEQ ID NO:2 under high stringency conditions; and those having substantial nucleic acid identity with the nucleic acid sequence of SEQ ID NO:2.

The invention includes variants and derivatives of the ManA polypeptides, including fusion proteins. For example, fusion proteins of the invention include ManA polypeptide fused to a heterologous protein or peptide that confers a desired function. The heterologous protein or peptide can facilitate purification, oligomerization, stabilization, or secretion of the ManA polypeptide, for example. As further examples, the heterologous polypeptide can provide enhanced activity, including catalytic or binding activity, for ManA polypeptides, where the enhancement is either additive or synergistic. A fusion protein of an embodiment of the invention can be produced, for example, from an expression construct containing a polynucleotide molecule encoding ManA polypeptide in frame with a polynucleotide molecule for the heterologous protein. Embodiments of the invention also comprise vectors, plasmids, expression systems, host cells, and the like, containing a ManA polynucleotide molecule. Genetic engineering methods for the production of ManA polypeptides of embodiments of the invention include expression of a polynucleotide molecule in cell free expression systems and in cellular hosts, according to known methods.

The invention further includes compositions containing a substantially purified ManA polypeptide of the invention and a carrier. Such compositions are administered to a biomass containing mannanase for the reduction or degradation of the mannanase or to produce useful oligosaccharides from hemicellulose.

The invention also provides reagents, compositions, and methods that are useful for analysis of ManA activity.

These and various other features as well as advantages which characterize the present invention will be apparent from a reading of the following detailed description and a review of the associated drawings.

The following Tables 4 and 5 includes sequences used in describing embodiments of the present invention. In Table 4, the abbreviations are as follows: CD, catalytic domain; CBD_II, carbohydrate binding domain type II; CBD_III, carbohydrate binding domain type III; and FN-III, fibronectin domain type III. When used herein, N* indicates a string of unknown nucleic acid units, and X* indicates a string of unknown amino acid units, for example about 50 or more. Table 4 includes approximate start and stop information for segments, and Table 5 includes amino acid sequence data for segments.

TABLE 4

Nucleotide and polypeptide segments.

| ManA Segment | base BEGIN | base END | Length, bp | aa BEGIN No. | aa | aa END No. | aa | Length, aa | SEQ ID No. (amino acid) | SEQ ID No. (nucleotide) |
|---|---|---|---|---|---|---|---|---|---|---|
| Total length | 1 | 2289 | 2289 | 1 | M | 762 | S | 762 | 1 | 2 |
| Signal (potential) | 1 | 108 | 108 | 1 | M | 36 | A | 36 | | |
| CD (GH5) | 109 | 1233 | 1125 | 37 | A | 411 | G | 375 | 3 | |
| CBD III | 1363 | 1824 | 462 | 455 | V | 608 | T | 154 | 4 | |
| CBD II | 1984 | 2286 | 303 | 662 | G | 762 | S | 101 | 5 | |

TABLE 5

Gene/polypeptide segments with amino acid sequences.

| SEQ ID No. (amino acid) | SEQ ID No. (nucleotide) | ManA Segment | segment data |
|---|---|---|---|
| 1 | 2 | Total length | SEQ ID NO:1 (see Table 1): SEQ ID NO:2 (see Table 2) |
| | | Signal (potential) | MGLVRRPARAFVATAAGTAVAAAATLGSITMPSATA |
| 3 | | CD (GH5) | APAGFVTASGGQFVLNGLPYRYGGTNNYYLSYQSHADVDDVLAKAQAMNLSVIRTWGFIDIGSL DGSVPTIDGNGFYFQYWDPSTGAPAYNDGPTGLQGLDYAIASAAAHGLRVIVVLTNDWKEFG |

TABLE 5-continued

Gene/polypeptide segments with amino acid sequences.

| SEQ ID No. (amino acid) | SEQ ID No. (nucleotide) | ManA Segment | segment data |
|---|---|---|---|
| | | | GMDQYDKWYGLPYHDNFYTDPRTQQAYKNWVNHLLNRVNSITGVTYKNDPTIFAWELANEPR |
| | | | CVGSGTLPTSGTCTQATIVNWVDQMSAYVKSIDPNHMVSVGDEGFYIGSTQGSGWPYNDPSDGV |
| | | | DNNALLRVKNIDFGTYHLYPNYWGQNADWGTQWIKDHIANAAAIGKPTILEEFGWQTPDRDSV |
| | | | YQTWTQTVRTNGEAGWNFWMLAGNVNGQPYPNYDGENVYYPSSTATVLASEALAISTG |
| 4 | | CBD III | VSGGVKVQYKNNDSAPGDNQIKPGLQLVNTGSSSVDLSTVTVRYWFTRDGGSSTLVYNCDWAA |
| | | | MGCGNIRASFGSVNPATPTADTYLQLSFTGGTLAAGGSTGEIQNRVNKSDWSNFDETNDYSYGT |
| | | | NTAFQDWTKVTVYVNGRLVWGTEPSGT |
| 5 | | CBD II | GVGCRATYVVNSDWGSGFTATVTVTNTGSRATSGWTVAWSFGGNQTVTNYWNTALTQSGASV |
| | | | TATNLSYNNVIQPGQSTTFGFNGSYSGTNTAPTLTCTAS |

DETAILED DESCRIPTION

Definitions

Figure 1:
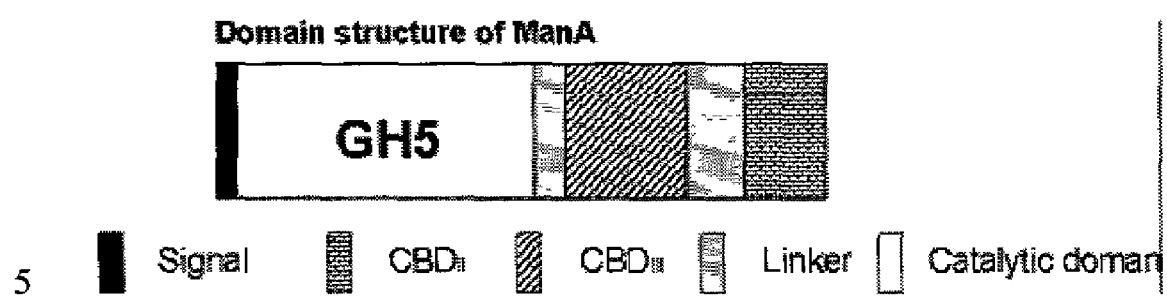
FIG. 1 is a schematic representation of the gene sequence and amino acid segment organization.

The following definitions are provided to facilitate understanding of certain terms used frequently herein and are not meant to limit the scope of the present disclosure:

"Amino acid" refers to any of the twenty naturally occuring amino acids as well as any modified amino acid sequences. Modifications may include natural processes such as posttranslational processing, or may include chemical modifications which are known in the art. Modifications include but are not limited to: phosphorylation, ubiquitination, acetylation, amidation, glycosylatioin, covalent attachment of flavin, ADP-ribosylation, cross linking, iodination, methylation, and alike.

"Antibody" refers to a Y-shaped molecule having a pair of antigen binding sites, a hinge region and a constant region. Fragments of antibodies, for example an antigen binding fragment (Fab), chimeric antibodies, antibodies having a human constant region coupled to a murine antigen binding region, and fragments thereof, as well as other well known recombinant antibodies are included in the present invention.

"Antisense" refers to polynucleotide sequences that are complementary to target "sense" polynucleotide sequence.

"Binding activity" refers to any activity that can be assayed by characterizing the ability of a polypeptide to bind to substrate. The substrate can be a carbohydrate polymer such as hemicellulose, including mannan, or can be a complex molecule or aggregate of molecules where the entire moiety comprises at least some carbohydrate.

"Complementary" or "complementarity" refers to the ability of a polynucleotide in a polynucleotide molecule to form a base pair with another polynucleotide in a second polynucleotide molecule. For example, the sequence A-G-T is complementary to the sequence T-C-A. Complementarity may be partial, in which only some of the polynucleotides match according to base pairing, or complete, where all the polynucleotides match according to base pairing.

"Expression" refers to transcription and translation occurring within a host cell. The level of expression of a DNA molecule in a host cell may be determined on the basis of either the amount of corresponding mRNA that is present within the cell or the amount of DNA molecule encoded protein produced by the host cell (Sambrook et al., 1989, *Molecular cloning: A Laboratory Manual*, 18.1–18.88).

"Fusion protein" refers to a first protein having attached a second, heterologous protein. Preferably, the heterologous protein is fused via recombinant DNA techniques, such that the first and second proteins are expressed in frame. The heterologous protein can confer a desired characteristic to the fusion protein, for example, a detection signal, enhanced stability or stabilization of the protein, facilitated oligomerization of the protein, or facilitated purification of the fusion protein. Examples of heterologous proteins useful in the fusion proteins of the invention include molecules having the catalytic domain of ManA, one or more binding domains of ManA, one or more catalytic domains of a glycoside hydrolase other than ManA, one or more binding domains of a glycoside hydrolase other than ManA, or any combination thereof. Further examples include immunoglobulin molecules and portions thereof, peptide tags such as histidine tag (6-His), leucine zipper, substrate targeting moieties, signal peptides, and the like. Fusion proteins are also meant to encompass variants and derivatives of ManA polypeptides that are generated by conventional site-directed mutagenesis and more modem techniques such as directed evolution, discussed infra.

"Genetically engineered" refers to any recombinant DNA or RNA method used to create a prokaryotic or eukaryotic host cell that expresses a protein at elevated levels, at lowered levels, or in a mutated form. In other words, the host cell has been transfected, transformed, or transduced with a recombinant polynucleotide molecule, and thereby been altered so as to cause the cell to alter expression of the desired protein. Methods and vectors for genetically engineering host cells are well known in the art; for example various techniques are illustrated in Current Protocols in Molecular Biology, Ausubel et al., eds. (Wiley & Sons, New York, 1988, and quarterly updates). Genetically engineering techniques include but are not limited to expression vectors, targeted homologous recombination and gene activation (see, for example, U.S. Pat. No. 5,272,071 to Chappel) and trans activation by engineered transcription factors (see, for example, Segal et al., 1999, *Proc Natl Acad Sci USA* 96(6):2758–63).

"Glycoside hydrolase family" refers to a family of enzymes, which hydrolyze the glycosidic bond between two or more carbohydrates or between a carbohydrate and a non-carbohydrate moiety (Henrissat B., (1991) Biochem. J., 280:309–316). Identification of a putative glycoside hydrolase family member is made based on an amino acid sequence comparison and the finding of significant sequence similarity within the putative member's catalytic domain, as compared to the catalytic domains of known family members.

"Homology" refers to a degree of complementarity between polynucleotides, having significant effect on the efficiency and strength of hybridization between polynucleotide molecules. The term also can refer to a degree of similarity between polypeptides.

"Host cell" or "host cells" refers to cells expressing a heterologous polynucleotide molecule. Host cells of the present invention express polynucleotides encoding ManA or a fragment thereof. Examples of suitable host cells useful in the present invention include, but are not limited to, prokaryotic and eukaryotic cells. Specific examples of such cells include bacteria of the genera *Escherichia*, *Bacillus*, and *Salmonella*, as well as members of the genera *Pseudomonas*, *Streptomyces*, and *Staphylococcus*; fungi, particularly filamentous fungi such as *Trichoderma* and *Aspergillus*, *Phanerochaete chrysosporium*, and other white rot fungi; also other fungi including *Fusaria*, molds and yeast including *Saccharomyces* sp., and *Candida* sp. and the like; plants e.g. *Arabidopsis*, cotton, barley, tobacco, potato, aquatic plants and the like; SF9 insect cells (Summers and Smith, 1987, *Texas Agriculture Experiment Station Bulletin*, 1555), and the like. Other specific examples include mammalian cells such as human embyonic kidney cells (293 cells), Chinese hamster ovary (CHO) cells (Puck et al., 1958, *Proc. Natl. Acad. Sci. USA* 60, 1275–1281), human cervical carcinoma cells (HELA) (ATCC CCL 2), human liver cells (Hep G2) (ATCC HB8065), human breast cancer cells (MCF-7) (ATCC HTB22), human colon carcinoma cells (DLD-1) (ATCC CCL 221), Daudi cells (ATCC CRL-213), murine myeloma cells such as P3/NSI/1-Ag4-1 (ATCC TIB-18), P3X63Ag8 (ATCC TIB-9), SP2/0-Ag14 (ATCC CRL-1581) and the like.

"Hybridization" refers to the pairing of complementary polynucleotides during an annealing period. The strength of hybridization between two polynucleotide molecules is impacted by the homology between the two molecules, stringency of the conditions involved, the melting temperature of the formed hybrid and the G:C ratio within the polynucleotides.

"Identity" refers to a comparison between pairs of nucleic acid or amino acid molecules. Methods for determining sequence identity are known. See, for example, computer programs commonly employed for this purpose, such as the Gap program (Wisconsin Sequence Analysis Package, Version 8 for Unix, Genetics Computer Group, University Research Park, Madison Wis.), that uses the algorithm of Smith and Waterman, 1981, *Adv. Appl. Math.*, 2: 482–489.

"Isolated" refers to a polynucleotide or polypeptide that has been separated from at least one contaminant (polynucleotide or polypeptide) with which it is normally associated. For example, an isolated polynucleotide or polypeptide is in a context or in a form that is different from that in which it is found in nature.

"Mannanase activity" refers to any activity that can be assayed by characterizing the enzymatic activity of a mannanase. For example, mannanase activity can be assayed by determining how much reducing sugar is produced during a fixed amount of time for a set amount of enzyme acting on mannan (see Irwin et al., (1998) *J. Bacteriology*, 1709–1714). Other assays are well known in the art and can be substituted, for example, by applying a solution to be tested for mannanase to a 1–4 mm diameter hole punched out in agar plates containing 0.2% AZCL galactomannan or other target mannan substrate.

"Nucleic acid sequence" refers to the order or sequence of deoxyribonucleotides along a strand of deoxyribonucleic acid. The order of these deoxyribonucleotides determines the order of amino acids along a polypeptide chain. The deoxyribonucleotide sequence thus codes for the amino acid sequence.

"Polynucleotide" refers to a linear sequence of nucleotides. The nucleotides may be ribonucleotides, or deoxyribonucleotides, or a mixture of both. Examples of polynucleotides in the context of the present invention include single and double stranded DNA, single and double stranded RNA, and hybrid molecules having mixtures of single and double stranded DNA and RNA. The polynucleotides of the present invention may contain one or more modified nucleotides.

"Protein," "peptide," and "polypeptide" are used interchangeably to denote an amino acid polymer or a set of two or more interacting or bound amino acid polymers.

"Purify," or "purified" refers to a target protein that is free from at least 5–10% of contaminating proteins. Purification of a protein from contaminating proteins can be accomplished using known techniques, including ammonium sulfate or ethanol precipitation, acid precipitation, heat precipitation, anion or cation exchange chromatography, phosphocellulose chromatography, hydrophobic interaction chromatography, affinity chromatography, hydroxylapatite chromatography, size-exclusion chromatography, and lectin chromatography. Various protein purification techniques are illustrated in *Current Protocols in Molecular Biology*, Ausubel et al., eds. (Wiley & Sons, New York, 1988, and quarterly updates).

"Selectable marker" refers to a marker that identifies a cell as having undergone a recombinant DNA or RNA event. Selectable markers include, for example, genes that encode antimetabolite resistance such as the DHFR protein that confers resistance to methotrexate (Wigler et al, 1980, *Proc Natl Acad Sci USA* 77:3567; O'Hare et al., 1981, *Proc Natl Acad Sci USA*, 78:1527), the GPT protein that confers resistance to mycophenolic acid (Mulligan & Berg, 1981, *PNAS USA*, 78:2072), the neomycin resistance marker that confers resistance to the aminoglycoside G-418 (Calberre-Garapin et al., 1981, *J. Mol Biol*, 150:1), the Hygro protein that confers resistance to hygromycin (Santerre et al., 1984, *Gene* 30:147), and the Zeocin™ resistance marker (Invitrogen). In addition, the herpes simplex virus thymidine kinase, hypoxanthine-guanine phosphoribosyltransferase and adenine phosphoribosyltransferase genes can be employed in tk$^-$, hgprt$^-$ and aprt$^-$ cells, respectively.

"Stringency" refers to the conditions (temperature, ionic strength, solvents, etc) under which hybridization between polynucleotides occurs. A hybridzation reaction conducted under high stringency conditions is one that will only occur between polynucleotide molecules that have a high degree of complementary base pairing (85% to 100% identity). Conditions for high stringency hybridization, for example, may include an overnight incubation at about 42° C. for about 2.5 hours in 6×SSC/0.1% SDS, followed by washing of the filters in 1.0×SSC at 65° C., 0.1% SDS. A hybridization reaction conducted under moderate stringency conditions is one that will occur between polynucleotide molecules that have an intermediate degree of complementary base pairing (50% to 84% identity).

"Substrate targeting moiety" refers to any signal on a substrate, either naturally occurring or genetically engineered, used to target any ManA polypeptide or fragment thereof to a substrate. Such targeting moieties include ligands that bind to a substrate structure. Examples of ligand/receptor pairs include carbohydrate binding domains and mannans. Many such substrate-specific ligands are known and are useful in the present invention to target a ManA polypeptide or fragment thereof to a substrate. A novel example is a ManA carbohydrate binding domain that is used to tether other molecules to a Mannan-containing substrate such as a fabric.

"Thermal tolerant" refers to the property of withstanding partial or complete inactivation by heat and can also be described as thermal resistance or thermal stability. Although some variation exists in the literature, the following definitions can be considered typical for the optimum temperature range of stability and activity for enzymes: psychrophilic (below freezing to 10° C.); mesophilic (10° C. to 50° C.); thermophilic (50° C. to 75° C.); and caldophilic (75° C. to above boiling water temperature). The stability and catalytic activity of enzymes are linked characteristics, and the ways of measuring these properties vary considerably. For industrial enzymes, stability and activity are best measured under use conditions, often in the presence of substrate. Therefore, mannanases that must act on process streams of mannans must be able to withstand exposure up to thermophilic or even caldophilic temperatures for digestion times in excess of several hours.

In encompassing a wide variety of potential applications for embodiments of the present invention, thermal tolerance refers to the ability to function in a temperature range of from about 15° C. to about 100° C. A preferred range is from about 30° C. to about 80° C. A highly preferred range is from about 50° C. to about 70° C. For example, a protein that can function at about 45° C. is considered in the preferred range even though it may be susceptible to partial or complete inactivation at temperatures in a range above about 45° C. and less than about 80° C. For polypeptides derived from organisms such as *Acidothermus*, the desirable property of thermal tolerance among is often accompanied by other desirable characteristics such as: resistance to extreme pH degradation, resistance to solvent degradation, resistance to proteolytic degradation, resistance to detergent degradation, resistance to oxidizing agent degradation, resistance to chaotropic agent degradation, and resistance to general degradation. Cowan D A in Danson M J et al. (1992) The *Archaebacteria, Biochemistry and Biotechnology* at 149–159, University Press, Cambridge, ISBN 1855780100. Here 'resistance' is intended to include any partial or complete level of residual activity. When a polypeptide is described as thermal tolerant it is understood that any one, more than one, or none of these other desirable properties can be present.

"Variant", as used herein, means a polynucleotide or polypeptide molecule that differs from a reference molecule. Variants can include nucleotide changes that result in amino acid substitutions, deletions, fusions, or truncations in the resulting variant polypeptide when compared to the reference polypeptide.

"Vector," "extra-chromosomal vector" or "expression vector" refers to a first polynucleotide molecule, usually double-stranded, which may have inserted into it a second polynucleotide molecule, for example a foreign or heterologous polynucleotide. The heterologous polynucleotide molecule may or may not be naturally found in the host cell, and may be, for example, one or more additional copy of the heterologous polynucleotide naturally present in the host genome. The vector is adapted for transporting the foreign polynucleotide molecule into a suitable host cell. Once in the host cell, the vector may be capable of integrating into the host cell chromosomes. The vector may optionally contain additional elements for selecting cells containing the integrated polynucleotide molecule as well as elements to promote transcription of mRNA from transfected DNA. Examples of vectors useful in the methods of the present invention include, but are not limited to, plasmids, bacteriophages, cosmids, retroviruses, and artificial chromosomes.

Within the application, unless otherwise stated, the techniques utilized may be found in any of several well-known references, such as: *Molecular Cloning: A Laboratory Manual* (Sambrook et al. (1989) Molecular cloning: A Laboratory Manual), *Gene Expression Technology* (Methods in Enzymology, Vol. 185, edited by D. Goeddel, 1991 Academic Press, San Diego, Calif.), "Guide to Protein Purification" in *Methods in Enzymology* (M. P. Deutshcer, 3d., (1990) Academic Press, Inc.), *PCR Protocols: A Guide to Methods and Applications* (Innis et al. (1990) Academic Press, San Diego, Calif.), Culture of Animal Cells: A Manual of Basic Technique, $2^{nd}$ ed. (R. I. Freshney (1987) Liss, Inc., New York, N.Y.), and *Gene Transfer and Expression Protocols*, pp 109–128, ed. E. J. Murray, The Humana Press Inc., Clifton, N.J.).

O-Glycoside Hydrolases

Figure 2:
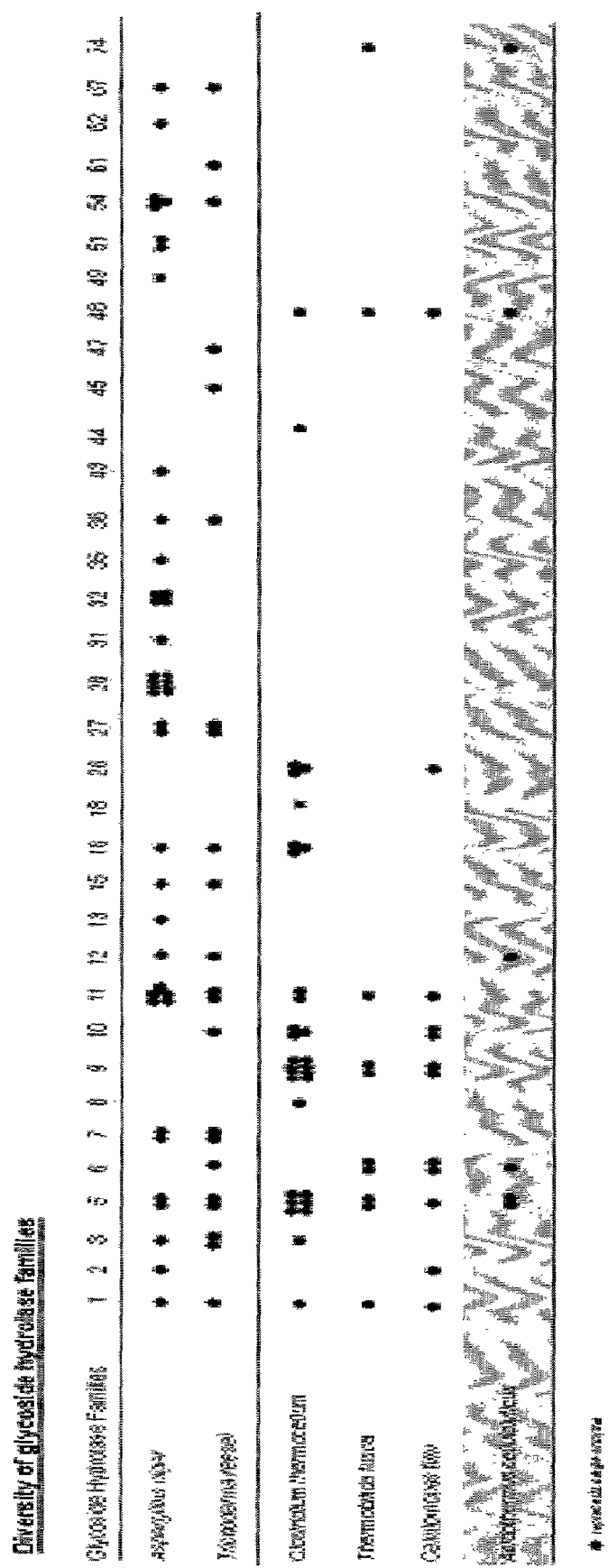
FIG. 2 is a graphic representation of the glycoside hydrolase gene/protein families found in various organisms.

Glycoside hydrolases are a large and diverse family of enzymes that hydrolyze the glycosidic bond between two carbohydrate moieties or between a carbohydrate and non-carbohydrate moiety (See FIG. 2). Glycoside hydrolase enzymes are classified into glycoside hydrolase (GH) families based on significant amino acid similarities within their catalytic domains, as compared to the catalytic domain of known family members. Enzymes having related catalytic domains are grouped together within a family (Henrissat et al., (1991) supra; Henrissat et al., (1996), *Biochem. J.* 316:695–696), where the underlying classification provides a direct relationship between the GH domain amino acid sequence and how the GH domain will fold. This information ultimately provides a common mechanism for how the enzyme will hydrolyze the glycosidic bond within a substrate, i.e., either by a retaining mechanism or inverting mechanism (Henrissat B., (1991) supra).

Mannanases belong to the GH family of enzymes. Mannanases are produced by a variety of bacteria and fungi to degrade the β-1,4 linkages in mannans, glucomannans, galactomannans, and galactoglucomannans and to so produce oligosaccharides. At present, mannanases are found within either the GH5 or GH26 family of glycoside hydrolases (Hilge et al., (1998) *Structure* 6(11):1433–1444).

Mannanases are characterized by having a multiple domain unit within their overall structure; a GH or catalytic domain is joined to a carbohydrate binding type II and III domains (CBD) by a glycosylated linker peptides (see FIG.

1) (Koivula et al., (1996) *Protein Expression and Purification* 8:391–400). The catalytic domain hydrolyzes the maiman, the CBD type domains increase the concentration of the enzyme on the substrate, in this case hemicellulose, and the linker peptides provide flexibility.

Conversion of hemicellulose to oligosaccharides by mannanases elevates the value of the complex substrate, such as in foods, feeds and paper pulp. For example, mannan polymers from the hemicellulose fraction of softwood are known to contaminate the cellulose fibers in paper pulp. Addition of a mannanases to the paper pulp can reduce the amounts of these contaminants and provide a higher quality product.

In addition, mannanase released oligosaccharides from hemicellulose may be used as bulking agents or stabilizers, for example mannan-oligomers released from palm seed mannan, in food or feeds.

Finally, mannanases can be useful in the production of biofuels from plant biomass, where the mannanases participate in the hydrolysis of the hemicellulose fraction to oligosaccharides, which can be further reduced to sugars and converted to ethanol via fermentation.

ManA

As described more fully in the Examples below, ManA, a novel thermostable mannanase, has now been identified and characterized. The predicted amino acid sequence of ManA (SEQ ID NO:1) has an organization characteristic of a mannanase enzyme. ManA contains a GH5 catalytic domain (about amino acid 37 to 411)-linker domain-carbohydrate binding type III domain (about amino acid 455 to 608) organization, as well as a second carbohydrate binding type II domain (about amino acid 662 to 762). As discussed in more detail below, significant amino acid similarity of ManA to other mannanases identifies ManA as a mannanase.

ManA, as noted above, has a catalytic domain belonging to the GH5 family of glycoside hydrolases. The GH5 domain family includes a number of β-mannanases, for example, β-mannanase isolated from *Agaricus bisporus*, and β-mannanase isolated from *Trichoderma reesei* (*Hypocrea jecorina*). The GH5 members degrade substrate using a retaining mechanism.

Being a mannanase member of the GH5 family of glycoside hydrolases identifies ManA as having β-mannanase (EC 3.2.1.78) activity. In addition, the predicted amino acid sequence (SEQ ID NO:1) indicates that CBD type II and CBD type III domains are present as characterized by Tomme P. et al. (1995), in Enzymatic Degradation of Insoluble Polysaccharides (Saddler J N & Penner M, eds.), at 142–163, American Chemical Society, Washington. See also Tomme, P. & Claeyssens, M. (1989) FEBS Lett. 243, 239–2431; Gilkes, N. R et al., (1988) J. Biol. Chem. 263, 10401–10407.

ManA is also a thermostable mannanase as it is produced by the thermophile *Acidothermus cellulolyticus*. ManA can have other thermostable associated characteristics—for example, resistance to acidity, resistance to protein degradation, and the like (Cowan D., (1992) supra). Like other members of the mannanase family, and in particular thermostable mannanases, ManA is useful in converting hemicellulose to oligosaccharides and thereby elevating the value of the complex substrate, for example in foods, feeds and paper pulp. Oligosaccharides produced by ManA may also be used as a bulking agent or stabilizer in foods and feeds. In addition, ManA is useful in the conversion of biofuels from biomass, and in particular, biofuels from hemicellulose. It is envisioned that ManA could be used alone or in combination with one or more other mannanase or other relevant glycoside hydrolase to perform the uses described herein or known within the relevant art, all of which are within the scope of the present disclosure.

ManA Polypeptides:

ManA polypeptides of the invention include isolated polypeptides having an amino acid sequence as shown below in Example 1; Table 1 and in SEQ ID NO:1, as well as variants and derivatives, including fragments, having substantial identity to the amino acid sequence of SEQ ID NO:1 and that retain any of the functional activities of ManA. ManA polypeptide activity can be determined, for example, by subjecting the variant, derivative, or fragment to a substrate binding assay or a mannanase activity assay such as those described for cellulases in Irwin D et al., J. Bacteriology 180(7): 1709–1714 (April 1998) or U.S. Pat. No. 6,060,299.

TABLE 1

ManA amino acid sequence (SEQ ID NO:1)
MGLVRRPARAFVATAAGTAVAAAATLGSITMPSATAAPAGFVTASGGQFV

LNGLPYRYGGTNNYYLSYQSHADVDDVLAKAQAMNLSVIRTWGFIDIGSL

DGSVPTIDGNKNGFYFQYWDPSTGAPAYNDGPTGLQGLDYAIASAAAHGL

RVIVVLTNDWKEFGGMDQYDKWYGLPYHDNFYTDPRTQQAYKNWVNHLLN

RVNSITGVTYKNDPTIFAWELANEPRCVGSGTLPTSGTCTQATIVNWVDQ

MSAYVKSIDPNHMVSVGDEGFYIGSTQGSGWPYNDPSDGVDNNALLRVKN

IDFGTYHLYPNYWGQNADWGTQWIKDHIANAAAIGKPTILEEFGWQTPDR

DSVYQTWTQTVRTNGEAGWNFWMLAGNVNGQPYPNYDGFNVYYPSSTATV

LASEALAISTGTSPPPSPSSSPSSSPSPSPSPSASPSASPSASSSPSPSP

SSSPVSGGVKVQYKNNDSAPGDNQIKPGLQLVNTGSSSVDLSTVTVRYWF

TRDGGSSTLVYNCDWAAMGCGNIRASFGSVNPATPTADTYLQLSFTGGTL

AAGGSTGEIQNRVNKSDWSNFDETNDYSYGTNTAFQDWTKVTVYVNGRLV

WGTEPSGTSPSPTPSPSPTPSPSPSPTPSPSSSPSPSPSPSPSPTPSPSP

SPSPSPSVSSSGVGCRATYVVNSDWGSGFTATVTVTNTGSRATSGWTVAW

SFGGNQTVTNYWNTALTQSGASVTATNLSYNNVIQPGQSTTFGFNGSYSG

TNTAPTLTCTAS

As listed and described in Tables 1 and 4, the isolated ManA polypeptide includes an N-terminal hydrophobic region that functions as a signal peptide, having an amino acid sequence that begins with M1 and extends to approximately A36; a catalytic domain having significant sequence similarity to a GH5 family domain that begins at about A37 and extends to about G411, a carbohydrate binding domain type III region that begins at about V455 and extends to about T608, and a carbohydrate binding domain type II that begins at about G662 and extends to about S762. Variants and derivatives of ManA include, for example, ManA polypeptides modified by covalent or aggregative conjugation with other chemical moieties, such as glycosyl groups, polyethylene glycol (PEG) groups, lipids, phosphate, acetyl groups, and the like.

The amino acid sequence of ManA polypeptides of the invention is preferably at least about 60% identical, more preferably at least about 70% identical, or in some embodiments at least about 90% identical, to the ManA amino acid sequence shown above in Table 1 and SEQ ID NO:1. The percentage identity, also termed homology (see definition above) can be readily determined, for example, by comparing the two polypeptide sequences using any of the computer programs commonly employed for this purpose, such as the Gap program (Wisconsin Sequence Analysis Package, Version 8 for Unix, Genetics Computer Group, University Research Park, Madison Wis.), which uses the algorithm of Smith and Waterman, 1981, *Adv. Appl. Math.* 2: 482–489.

Variants and derivatives of the ManA polypeptide may further include, for example, fusion proteins formed of a ManA polypeptide and a heterologous polypeptide. Preferred heterologous polypeptides include those that facilitate purification, oligomerization, stability, or secretion of the ManA polypeptides.

Fragments of the ManA polypeptide may include, but are not limited to, the GH5 catalytic domain (SEQ ID NO:3), the carbohydrate binding domain type III (SEQ ID NO:4) and the carbohydrate binding domain type II (SEQ ID NO:5).

ManA polypeptide variants and derivatives, as used in the description of the invention, can contain conservatively substituted amino acids, meaning that one or more amino acid can be replaced by an amino acid that does not alter the secondary and/or tertiary structure of the polypeptide. Such substitutions can include the replacement of an amino acid, by a residue having similar physicochemical properties, such as substituting one aliphatic residue (Ile, Val, Leu, or Ala) for another, or substitutions between basic residues Lys and Arg, acidic residues Glu and Asp, amide residues Gln and Asn, hydroxyl residues Ser and Tyr, or aromatic residues Phe and Tyr. Phenotypically silent amino acid exchanges are described more fully in Bowie et al., 1990, *Science* 247: 1306–1310. In addition, functional ManA polypeptide variants include those having amino acid substitutions, deletions, or additions to the amino acid sequence outside functional regions of the protein, for example, outside the catalytic and carbohydrate binding domains. These would include, for example, the various linker sequences that connect functional domains as defined herein.

The ManA polypeptides of the present invention are preferably provided in an isolated form, and preferably are substantially purified. The polypeptides may be recovered and purified from recombinant cell cultures by known methods, including, for example, ammonium sulfate or ethanol precipitation, anion or cation exchange chromatography, phosphocellulose chromatography, hydrophobic interaction chromatography, affinity chromatography, hydroxylapatite chromatography, and lectin chromatography. Preferably, high performance liquid chromatography (HPLC) is employed for purification.

Another preferred form of ManA polypeptides is that of recombinant polypeptides as expressed by suitable hosts. Furthermore, the hosts can simultaneously produce other mannanases or glycoside hydrolases such that a mixture is produced comprising a ManA polypeptide and one or more other glycoside hydrolases. Such a mixture can be effective in crude fermentation processing or other industrial processing (see below).

ManA polypeptides can be fused to heterologous polypeptides to facilitate purification. Many available heterologous peptides (peptide tags) allow selective binding of the fusion protein to a binding partner. Non-limiting examples of peptide tags include 6-His, thioredoxin, hemaglutinin, GST, and the OmpA signal sequence tag. A binding partner that recognizes and binds to the heterologous peptide can be any molecule or compound, including metal ions (for example, metal affinity columns), antibodies, antibody fragments, or any protein or peptide that preferentially binds the heterologous peptide to permit purification of the fusion protein.

ManA polypeptides can be modified to facilitate formation of ManA oligomers. For example, ManA polypeptides can be fused to peptide moieties that promote oligomerization, such as leucine zippers and certain antibody fragment polypeptides, for example, Fc polypeptides. Techniques for preparing these fusion proteins are known, and are described, for example, in WO 99/31241 and in Cosman et.al., 2001 *Immunity* 14:123–133. Fusion to an Fc polypeptide offers the additional advantage of facilitating purification by affinity chromatography over Protein A or Protein G columns. Fusion to a leucine-zipper (LZ), for example, a repetitive heptad repeat, often with four or five leucine residues interspersed with other amino acids, is described in Landschultz et al., 1988, *Science*, 240:1759.

It is also envisioned that an expanded set of variants and derivatives of ManA polynucleotides and/or polypeptides can be generated to select for useful molecules, where such expansion is achieved not only by conventional methods such as site-directed mutagenesis (SDM) but also by more modern techniques, either independently or in combination.

Site-directed-mutagenesis is considered an informational approach to protein engineering and can rely on high-resolution crystallographic structures of target proteins and some stratagem for specific amino acid changes (Van Den Burg, B.; Vriend, G.; Veltman, O. R.; Venema, G.; Eijsink, V. G. H. Proc. Nat. Acad. Sci. U.S. 1998, 95, 2056–2060). For example, modification of the amino acid sequence of ManA polypeptides can be accomplished as is known in the art, such as by introducing mutations at particular locations by oligonucleotide-directed mutagenesis (Walder et al., 1986, Gene, 42:133; Bauer et al., 1985, Gene 37:73; Craik, 1985, BioTechniques, 12–19; Smith et al., 1981, Genetic Engineering: Principles and Methods, Plenum Press; and U.S. Pat. No. 4,518,584 and U.S. Pat. No. 4,737,462). SDM technology can also employ the recent advent of computational methods for identifying site-specific changes for a variety of protein engineering objectives (Hellinga, H. W. Nature Structural. Biol. 1998, 5, 525–527).

The more modern techniques include, but are not limited to, non-informational mutagenesis techniques (referred to generically as "directed evolution"). Directed evolution, in conjunction with high-throughput screening, allows testing of statistically meaningful variations in protein conformation (Arnold, F. H. Nature Biotechnol. 1998, 16, 617–618). Directed evolution technology can include diversification methods similar to that described by Crameri A. et al. (1998, Nature 391: 288–291), site-saturation mutagenesis, staggered extension process (StEP) (Zhao, H.; Giver, L.; Shao, Z.; Affholter, J. A.; Arnold, F. H. Nature Biotechnol. 1998, 16, 258–262), and DNA synthesis/reassembly (U.S. Pat. No. 5,965,408).

Fragments of the ManA polypeptide can be used, for example, to generate specific anti-ManA antibodies. Using known selection techniques, specific epitopes can be selected and used to generate monoclonal or polyclonal antibodies. Such antibodies have utlilty in the assay of ManA activity as well as in purifying recombinant ManA polypeptides from genetically engineered host cells.

ManA Polynucleotides:

The invention also provides polynucleotide molecules encoding the ManA polypeptides discussed above. ManA polynucleotide molecules of the invention include polynucleotide molecules having the nucleic acid sequence shown in Table 2 and SEQ ID NO:2, polynucleotide molecules that hybridize to the nucleic acid sequence of Table 2 and SEQ ID NO:2 under high stringency hybridization conditions (for example, 42°, 2.5 hr., 6×SCC, 0.1% SDS); and polynucleotide molecules having substantial nucleic acid sequence identity with the nucleic acid sequence of Table 2 and SEQ ID NO:2, particularly with those nucleic acids encoding the catalytic domain, GH5 (from amino acid 37 to 411), the carbohydrate binding domain III (from amino acid 455 to 608) and carbohydrate binding domain II (from amino acid 662 to 762).

TABLE 2

ManA nucleotide sequence.
(SEQ ID NO:2)

ATGGGTCTAGTGCGTCGCCCTGCGCGAGCATTTGTTGCGACCGCGGCCGG

CACTGCCGTTGCTGCCGCGGCGACGCTCGGCTCAATCACCATGCCGTCAG

CCACGGCAGCGCCGGCGGGATTCGTCACCGCATCCGGCGGTCAGTTCGTT

CTGAACGGCCTTCCCTATCGTTACGGGGAACGAACAACTATTACCTCAG

CTATCAGTCGCACGCCGACGTCGATGACGTGTTGGCCAAGGCTCAAGCGA

TGAATCTTTCTGTCATCCGGACCTGGGGTTTCATCGACATCGGCTCTCTT

GACGGCTCCGTGCCCACAATCGATGGCAACAAGAACGGCTTCTACTTTCA

GTACTGGGACCCGTCGACCGGCGCTCCGGCGTACAACGACGGGCCGACCG

GCTTGCAAGGCCTTGACTACGCGATCGCGAGCGCGGCCGCGCACGGCCTT

CGGGTGATTGTCGTCCTCACCAACGACTGGAAAGAATTTGGGGGAATGGA

TCAATACGACAAGTGGTACGGCCTTCCTTACCACGACAACTTCTACACCG

ACCCCCGGACCCAGCAGGCGTACAAGAATTGGGTCAATCATCTACTGAAC

CGGGTCAACAGCATTACCGGCGTGACGTACAAGAACGATCCAACGATCTT

TGCTTGGGAACTTGCCAATGAGCCGCGCTGCGTAGGAAGCGGCACATTAC

CAACCTCGGGCACGTGCACTCAGGCGACCATTGTCAACTGGGTCGATCAA

ATGTCGGCGTACGTCAAAAGCATAGACCCTAACCATATGGTCTCGGTCGG

CGACGAAGGGTTCTACATTGGGTCAACGCAGGGAAGCGGCTGGCCATACA

ACGACCCGTCCGACGGCGTCGACAACAATGCTCTTCTCCGTGTCAAGAAC

ATTGACTTTGGCACGTATCACCTGTACCCGAATTACTGGGGCCAGAACGC

GGACTGGGGAACGCAATGGATCAAGGATCATATTGCGAATGCCGCAGCGA

TCGGCAAGCCGACCATTCTCGAAGAATTCGGCTGGCAGACACCGGACCGC

GATTCCGTCTATCAGACGTGGACCCAGACTGTGCGTACGAACGGTGAAGC

AGGCTGGAACTTCTGGATGCTCGCTGGGAATGTCAACGGCCAGCCATATC

CGAACTATGACGGCTTCAACGTCTACTACCCAAGTTCAACAGCGACCGTC

CTCGCCAGCGAGGCGCTCGCAATCAGTACCGGCACATCGCCTCCGCCGTC

GCCGAGCTCGAGTCCATCCTCGTCGCCGTCTCCGTCGCCGTCTCCGTCGG

CGTCTCCGTCGGCGTCTCCGTCGGCGTCTTCGTCGCCGAGCCCGTCTCCG

TCGTCGTCGCCGGTGTCGGGTGGGGTGAAGGTGCAGTACAAGAACAATGA

TTCGGCGCCGGGTGATAACCAGATCAAACCGGGTCTCCAGTTGGTGAATA

CGGGGTCGTCGTCGGTGGATTTGTCGACGGTGACGGTGCGGTACTGGTTC

ACCCGGGATGGTGGGTCGTCGACACTGGTGTACAACTGTGACTGGGCGGC

GATGGGGTGTGGGAATATCCGCGCCTCGTTCGGCTCGGTGAACCCGGCGA

CGCCGACGGCGGACACCTACCTGCAGTTGTCGTTCACTGGTGGAACGTTG

GCCGCTGGTGGGTCGACGGGTGAGATTCAAAACCGGGTGAATAAGAGTGA

CTGGTCGAACTTTGATGAGACCAATGACTACTCGTATGGGACGAACACCG

CCTTCCAGGATTGGACGAAGGTGACGGTGTATGTCAATGGCCGGCTGGTG

TGGGGGACTGAACCGTCCGGCACCAGCCCCAGCCCCACACCCAGCCCCAG

CCCAACCCCGTCCCCGAGCCCGAGCCCGACCCCAAGCCCCAGCTCCTCCC

CATCCCCGTCCCCGAGCCCCAGCCCCAGCCCTACGCCGTCCCCGTCGCCG

AGCCCGTCGCCGTCGCCGAGTGTGTCGTCGTCGGGTGTGGGGTGCCGGGC

GACGTATGTGGTGAATAGTGATTGGGGTTCTGGGTTTACGGCGACGGTGA

CGGTGACGAATACCGGGAGCCGGGCGACGAGCGGGTGGACGGTGGCGTGG

TCGTTTGGTGGGAATCAGACGGTCACGAACTACTGGAACACTGCGTTGAC

CCAATCAGGTGCATCGGTGACGGCGACGAACCTGAGCTACAACAACGTGA

TCCAACCGGGTCAGTCGACCACCTTCGGATTCAACGGAAGTTACTCAGGA

ACAAACACCGCACCTACACTCACCTGCACGGCTAGTTGA

The ManA polynucleotide molecules of the invention are preferably isolated molecules encoding the ManA polypeptide having an amino acid sequence as shown in Table 1 and SEQ ID NO:1, as well as derivatives, variants, and useful fragments of the ManA polynucleotide. The ManA polynucleotide sequence can include deletions, substitutions, or additions to the nucleic acid sequence of Table 2 and SEQ ID NO:2.

The ManA polynucleotide molecule of the invention can be cDNA, chemically synthesized DNA, DNA amplified by PCR, RNA, or combinations thereof. Due to the degeneracy of the genetic code, two DNA sequences may differ and yet encode identical amino acid sequences. The present invention thus provides an isolated polynucleotide molecule having a ManA nucleic acid sequence encoding ManA polypeptide, where the nucleic acid sequence encodes a polypeptide having the complete amino acid sequences as shown in Table 1 and SEQ ID NO:1, or variants, derivatives, and fragments thereof.

The ManA polynucleotides of the invention have a nucleic acid sequence that is at least about 60% identical to the nucleic acid sequence shown in Table 2 and SEQ ID NO:2, in some embodiments at least about 70% identical to the nucleic acid sequence shown in Table 2 and SEQ ID NO:2, and in other embodiments at least about 90% identical to the nucleic acid sequence shown in Table 2 and SEQ ID NO:2. Nucleic acid sequence identity is determined by known methods, for example by aligning two sequences in a software program such as the BLAST program (Altschul, S. F et al. (1990) J. Mol. Biol. 215:403–410, from the National Center for Biotechnology Information (http://www.ncbi.nlm.nih.gov/BLAST/).

The ManA polynucleotide molecules of the invention also include isolated polynucleotide molecules having a nucleic acid sequence that hybridizes under high stringency conditions (as defined above) to a the nucleic acid sequence shown in Table 2 and SEQ ID NO:2. Hybridization of the polynucleotide is to at least about 15 contiguous nucleotides, or at least about 20 contiguous nucleotides, and in other embodiments at least about 30 contiguous nucleotides, and in still other embodiments at least about 100 contiguous nucleotides of the nucleic acid sequence shown in Table 2 and SEQ ID NO:2.

Useful fragments of the ManA-encoding polynucleotide molecules described herein, include probes and primers. Such probes and primers can be used, for example, in PCR methods to amplify and detect the presence of ManA polynucleotides in vitro, as well as in Southern and Northern blots for analysis of ManA. Cells expressing the ManA polynucleotide molecules of the invention can also be identified by the use of such probes. Methods for the production and use of such primers and probes are known. For PCR, 5' and 3' primers corresponding to a region at the termini of the ManA polynucleotide molecule can be employed to isolate and amplify the ManA polynucleotide using conventional techniques.

Other useful fragments of the ManA polynucleotides include antisense or sense oligonucleotides comprising a single-stranded nucleic acid sequence capable of binding to a target ManA mRNA (using a sense strand), or DNA (using an antisense strand) sequence.

Vectors and Host Cells

The present invention also provides vectors containing the polynucleotide molecules of the invention, as well as host cells transformed with such vectors. Any of the polynucleotide molecules of the invention may be contained in a vector, which generally includes a selectable marker and an origin of replication, for propagation in a host. The vectors further include suitable transcriptional or translational regulatory sequences, such as those derived from a mammalian, microbial, viral, or insect genes, operably linked to the ManA polynucleotide molecule. Examples of such regulatory sequences include transcriptional promoters, operators, or enhancers, mRNA ribosomal binding sites, and appropriate sequences which control transcription and translation. Nucleotide sequences are operably linked when the regulatory sequence functionally relates to the DNA encoding the target protein. Thus, a promoter nucleotide sequence is operably linked to a ManA DNA sequence if the promoter nucleotide sequence directs the transcription of the ManA sequence.

Selection of suitable vectors for the cloning of ManA polynucleotide molecules encoding the target ManA polypeptides of this invention will depend upon the host cell in which the vector will be transformed, and, where applicable, the host cell from which the target polypeptide is to be expressed. Suitable host cells for expression of ManA polypeptides include prokaryotes, yeast, and higher eukaryotic cells, each of which is discussed below.

The ManA polypeptides to be expressed in such host cells may also be fusion proteins that include regions from heterologous proteins. As discussed above, such regions may be included to allow, for example, secretion, improved stability, or facilitated purification of the ManA polypeptide. For example, a nucleic acid sequence encoding an appropriate signal peptide can be incorporated into an expression vector. A nucleic acid sequence encoding a signal peptide (secretory leader) may be fused in-frame to the ManA sequence so that ManA is translated as a fusion protein comprising the signal peptide. A signal peptide that is functional in the intended host cell promotes extracellular secretion of the ManA polypeptide. Preferably, the signal sequence will be cleaved from the ManA polypeptide upon secretion of ManA from the cell. Non-limiting examples of signal sequences that can be used in practicing the invention include the yeast I-factor and the honeybee melatin leader in Sf9 insect cells.

Suitable host cells for expression of target polypeptides of the invention include prokaryotes, yeast, and higher eukaryotic cells. Suitable prokaryotic hosts to be used for the expression of these polypeptides include bacteria of the genera *Escherichia, Bacillus*, and *Salmonella*, as well as members of the genera *Pseudomonas, Streptomyces*, and *Staphylococcus*. For expression in prokaryotic cells, for example, in *E. coli*, the polynucleotide molecule encoding ManA polypeptide preferably includes an N-terminal methionine residue to facilitate expression of the recombinant polypeptide. The N-terminal Met may optionally be cleaved from the expressed polypeptide.

Expression vectors for use in prokaryotic hosts generally comprise one or more phenotypic selectable marker genes. Such genes encode, for example, a protein that confers antibiotic resistance or that supplies an auxotrophic requirement. A wide variety of such vectors are readily available from commercial sources. Examples include pSPORT vectors, pGEM vectors (Promega, Madison, Wis.), pPROEX vectors (LTI, Bethesda, Md.), Bluescript vectors (Stratagene), and pQE vectors (Qiagen).

ManA can also be expressed in yeast host cells from genera including *Saccharomyces, Pichia*, and *Kluveromyces*. Preferred yeast hosts are *S. cerevisiae* and *P. pastoris*. Yeast vectors will often contain an origin of replication sequence from a 2T yeast plasmid, an autonomously replicating sequence (ARS), a promoter region, sequences for polyadenylation, sequences for transcription termination, and a selectable marker gene. Vectors replicable in both yeast and *E. coli* (termed shuttle vectors) may also be used. In addition to the above-mentioned features of yeast vectors, a shuttle vector will also include sequences for replication and selection in *E. coli*. Direct secretion of the target polypeptides expressed in yeast hosts may be accomplished by the inclusion of nucleotide sequence encoding the yeast I-factor leader sequence at the 5' end of the ManA-encoding nucleotide sequence.

Insect host cell culture systems can also be used for the expression of ManA polypeptides. The target polypeptides of the invention are preferably expressed using a baculovirus expression system, as described, for example, in the review by Luckow and Summers, 1988 *Bio/Technology* 6:47.

The choice of a suitable expression vector for expression of ManA polypeptides of the invention will depend upon the host cell to be used. Examples of suitable expression vectors for *E. coli* include pET, pUC, and similar vectors as is known in the art. Preferred vectors for expression of the ManA polypeptides include the shuttle plasmid pIJ702 for *Streptomyces lividans*, pGAPalpha-A, B, C and pPICZalpha-A, B, C (Invitorgen) for *Pichia pastoris*, and pFE-1 and pFE-2 for filamentous fungi and similar vectors as is known in the art.

Modification of a ManA polynucleotide molecule to facilitate insertion into a particular vector (for example, by modifying restriction sites), ease of use in a particular expression system or host (for example, using preferred host codons), and the like, are known and are contemplated for use in the invention. Genetic engineering methods for the production of ManA polypeptides include the expression of the polynucleotide molecules in cell free expression systems, in cellular hosts, in tissues, and in animal models, according to known methods.

Compositions

The invention provides compositions containing a substantially purified ManA polypeptide of the invention and an acceptable carrier. Such compositions are administered to biomass, for example, to degrade the hemicellulose in the biomass into simpler carbohydrate units and ultimately, to sugars. These released sugars from the hemicellulose are converted into ethanol by any number of different catalysts. Such compositions may also be included in detergents for removal, for example, of hemicellulose containing stains within fabrics, or compositions used in the pulp and paper industry to address conditions associated with hemicellulose contamination of the cellulose fraction. Compositions of the present invention can be used in degrading the hemicellulose fraction in the food and feed industry to result in a lower content of hemicellulose in food or feed. Compositions of the present invention can also be used to produce oligosaccharide bulking agents and stabilizers from hemicellulose for use in the food and feed industry. Compositions of the present invention that include either the carbohydrate binding domain type III or II polypeptides can be used as linking agents, for example, to link a target molecule fused to the CBD II or III to a carbohydrate containing target, including pharmaceutical compositions where the CBD II or III is used to target drugs to target carbohydrate expressing cells (see below).

The invention provides pharmaceutical compositions containing a substantially purified ManA polypeptide of the invention and if necessary a pharmaceutically acceptable carrier. Such pharmaceutical compositions are administered to cells, tissues, or patients, for example, to aid in delivery or targeting of other pharmaceutical compositions. For example, ManA polypeptides, and in particular the carbohydrate binding domains of ManA, may be used where carbohydrate-mediated liposomal interactions are involved with target cells. Vyas S P et al. (2001), *J. Pharmacy & Pharmaceutical Sciences* May–August 4(2): 138–58.

The invention also provides reagents, compositions, and methods that are useful for analysis of ManA activity and for the analysis of hemicellulose breakdown.

Compositions of the present invention may also include other known glycoside hydrolases, and preferably, other known thermal tolerant glycoside hydrolases for enhanced treatment of hemicellulose.

Antibodies

The polypeptides of the present invention, in whole or in part, may be used to raise polyclonal and monoclonal antibodies that are useful in purifying ManA, or detecting ManA polypeptide expression, as well as a reagent tool for characterizing the molecular actions of the ManA polypeptide. Preferably, a peptide containing a unique epitope of the ManA polypeptide is used in preparation of antibodies, using conventional techniques. Methods for the selection of peptide epitopes and production of antibodies are known. See, for example, *Antibodies: A Laboratory Manual*, Harlow and Land (eds.), 1988 Cold Spring Harbor Laboratory Press, Cold Spring Harbor, N.Y.; *Monoclonal Antibodies, Hybridomas: A New Dimension in Biological Analyses*, Kennet et al. (eds.), 1980 Plenum Press, New York.

Assays

Agents that modify, for example, increase or decrease, ManA hydrolysis or degradation of hemicellulose can be identified, for example, by assay of ManA mannanase activity and/or analysis of ManA binding to a carbohydrate substrate. Incubation of hemicellulose in the presence of ManA and in the presence or absence of a test agent and correlation of mannanase activity or carbohydrate binding permits screening of such agents. For example, mannanase activity and binding assays may be performed in a manner similar to those described for cellulases in Irwin et al., *J. Bacteriology* 180(7): 1709–1714 (April 1998).

The ManA stimulated activity is determined in the presence and absence of a test agent and then compared. A lower ManA activated test activity in the presence of the test agent, than in the absence of the test agent, indicates that the test agent has decreased the activity of the ManA. A higher ManA activated test activity in the presence of the test agent than in the absence of the test agent indicates that the test agent has increased the activity of the ManA. Stimulators and inhibitors of ManA may be used to augment, inhibit, or modify ManA mediated activity, and therefore may have potential industrial uses as well as potential use in the further elucidation of ManA's molecular actions.

Therapeutic Applications

The ManA polypeptides of the invention are effective in adding in delivery or targeting of other pharmaceutical compositions within a host. For example, ManA polypeptides, and in particular the ManA carbohydrate binding domains, may be used where carbohydrate-mediated liposomal interactions are involved with target cells. Vyas S P et al. (2001), *J. Pharm Pharm Sci* May–August 4(2): 138–58.

ManA polynucleotides and polypeptides, including vectors expressing ManA, of the invention can be formulated as pharmaceutical compositions and administered to a host, preferably mammalian host, including a human patient, in a variety of forms adapted to the chosen route of administration. The compounds are preferably administered in combination with a pharmaceutically acceptable carrier, and may be combined with or conjugated to specific delivery agents, including targeting antibodies and/or cytokines.

ManA can be administered by known techniques, such as orally, parentally (including subcutaneous injection, intravenous, intramuscular, intrasternal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, such as sterile injectable aqueous or oleagenous suspensions or suppositories.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Preferred administration routes include orally, parenterally, as well as intravenous, intramuscular or subcutaneous routes. More preferably, the compounds of the present invention are administered parenterally, i.e., intravenously or intraperitoneally, by infusion or injection.

Solutions or suspensions of the compounds can be prepared in water, isotonic saline (PBS) and optionally mixed with a nontoxic surfactant. Dispersions may also be prepared in glycerol, liquid polyethylene, glycols, DNA, vegetable oils, triacetin and mixtures thereof. Under ordinary conditions of storage and use, these preparations may contain a preservative to prevent the growth of microorganisms.

The pharmaceutical dosage form suitable for injection or infusion use can include sterile, aqueous solutions or dispersions or sterile powders comprising an active ingredient which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. The proper fluidity can be maintained, for example, by the formation of liposomes, by the maintenance of the required particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption—for example, aluminum monosterate hydrogels and gelatin.

Sterile injectable solutions are prepared by incorporating the compounds in the required amount in the appropriate solvent with various other ingredients as enumerated above and, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

INDUSTRIAL APPLICATIONS

The ManA polypeptides of the invention are effective thermostable mannanases. In the methods of the invention, the mannanase degrading effects of ManA are achieved by treating biomass at a ratio of about 1 to about 50 of ManA:biomass. ManA may be used under extreme conditions, for example, elevated temperatures and acidic pH. Treated biomass is degraded into simpler forms of carbohydrates, which is then used in the formation of ethanol or other industrial chemicals, as is known in the art. Other methods are envisioned to be within the scope of the present invention, including methods for treating fabrics to remove hemicellulose-containing stains and other methods already discussed. In addition, ManA polypeptides can be used to degrade the hemicellulose content of a substrate source in the food, feed and paper pulp industries, or alternatively, be used to produce useful oligosaccharides to be added to food and feed as bulking agents or stabilizing agents. ManA polypeptides can be used in any known application currently utilizing a mannanases, all of which are within the scope of the present invention. Having generally described the invention, the same will be more readily understood by reference to the following examples, which are provided by way of illustration and are not intended as limiting.

EXAMPLES

Example 1

Molecular Cloning of ManA

Genomic DNA was isolated from *Acidothermus cellulolyticus* and purified by banding on cesium chloride gradients. Genomic DNA was partially digested with Sau 3A and separated on agarose gels. DNA fragments in the range of 9–20 kilobase pairs were isolated from the gels. This purified Sau 3A digested genomic DNA was ligated into the Bam H1 acceptor site of purified EMBL3 lambda phage arms (Clontech, San Diego, Calif.). Phage DNA was packaged according to the manufacturer's specifications and plated with *E. coli* LE392 in top agar which contained the soluble cellulose analog, carboxymethylcellulose (CMC). The plates were incubated overnight (12–24 hours) to allow transfection, bacterial growth, and plaque formation. Plates were stained with Congo Red followed by destaining with 1 M NaCl. Lambda plaques harboring endoglucanase clones showed up as unstained plaques on a red background.

Lambda clones which screened positive on CMC-Congo Red plates were purified by successive rounds of picking, plating and screening. Individual phage isolates were named SL-1, SL-2, SL-3 and SL-4. Subsequent subcloning efforts employed the SL-3 clone which contained an approximately 14.2 kb fragment of *A. cellulolyticus* genomic DNA.

Template DNA was constructed using a 9 kb BamH1 fragment obtained from the 14.2 kb lambda clone SL3 prepared from *Acidothermus cellulolyticus* genomic DNA. The 9-kb BamHI fragment from SL3 was subcloned into pDR540 to generate a plasmid NREL501. NREL501 was first sequenced by the primer walking method as is known in the art. NREL501 was then subcloned into pUC19 using restriction enzymes PstI and EcoRI and transformed into *E. coli* XL1-blue (Stratagene, La Jolla, Calif.) for the production of template DNA for sequencing. Each subclone was sequenced from both forward and reverse directions. DNA for sequencing was prepared from an overnight growth in 500 mL LB broth using a megaprep DNA purification kit from Promega. The template DNA was PEG precipitated and suspended in de-ionized water and adjusted to a final concentration of 0.25 mg/mL.

Custom primers were designed by reading upstream known sequence and selecting segments of an appropriate length to function, as is well known in the art. Primers for cycle sequencing were synthesized at the Macromolecular Resources facility located at Colorado State University in Fort Collins, Colo. Typically the sequencing primers were 26–30 nucleotides in length, but were sometimes longer or shorter to accommodate a melting temperature appropriate for cycle sequencing. The sequencing primers were diluted in de-ionized water, the concentration measured using UV absorbance at 260 nm, and then adjusted to a final concentration of 5 pmol/μL.

Templates and sequencing primers were shipped to the Iowa State University DNA Sequencing facility at Ames, Iowa for sequencing using standard chemistries for cycle sequencing. In some cases, regions of the template that sequenced poorly using the standard protocols and dye terminators were repeated with the addition of 2 μL DMSO and by using nucleotides optimized for the sequencing of high GC content DNA. The high frequency of reoccurring small domains, i.e., CBDs and linkers, with high sequence similarity caused initial difficulties in sequence assignments which were only resolved through extensive review of the data and repeated analysis.

Sequencing data from primer walking and subclones were assembled together to verify that all SL3 regions had been sequenced from both strands. An open reading frames (ORF) was found in the 9-kb BamHI fragment, C-terminal of E1 (U.S. Pat. No. 5,536,655), termed ManA.

An ORF of 2289 bp [SEQ ID NO: 2] and deduced amino acid sequence [SEQ ID NO: 1] are shown in Tables 2 and 1, respectively. The amino acid sequence predicted by SEQ ID NO: 1 was determined to have significant homology to known mannanases, as shown below in Example 2 and in Table 3.

The amino acid sequence represents a novel member of the family of proteins with mannanase activity. Due to the source of isolation from the thermophilic organism *Acidothermus*, ManA is a novel member of the mannanase family with properties including thermal tolerance. It is also known that thermal tolerant enzymes may have other properties (see definition above).

Example 2

ManA Includes a GH5 Catalytic Domain

Sequence alignments and comparisons of the amino acid sequences of the *Acidothermus cellulolyticus* ManA catalytic domain (aa 37 to 411), *Agaricus bisporus* (β-mannanase) and *Trichoderma reesei* (β-mannanase) polypeptides were prepared, using the ClustalW program (Thompson J. D et al. (1994), Nucleic Acids Res. 22:4673–4680 from EMBL European Bioinformatics Institute website (http://www.ebi.ac.uk/).

An examination of the amino acid sequence alignment of the GH5 domains indicates that the amino acid sequence of the ManA catalytic domain is homologous to the amino acid sequences of known GH5 family catalytic domains for *A. bisporus* β-mannanase and *T. reesei* β-mannanase (See Table 3). In Table 3, the notations are as follows: an asterisk "*" indicates identical or conserved residues in all sequences in the alignment; a colon ":" indicates conserved substitutions; a period "." indicates semi-conserved substitutions; and a hyphen "-" indicates a gap in the sequence. The amino acid sequence predicted for the ManA GH5 domain is approximately 39% identical to the *A. bisporus* β-mannanase GH5 domain and approximately 35% identical to the *T. reesei* β-mannanase GH5 domain, indicating that the ManA catalytic domain is a member of the GH5 family (Henrissat et al. (1991), supra).

Table 3

Multiple amino acid sequence alignment of a ManA catalytic domain and polypeptides with Glycoside Hydrolase Family 5 catalytic domains.

```
Multialignment of related Glycoside Hydrolase Family 5 catalytic domain
GH5_Ace: Acidothermus cellulolyticus ManA catalytic domain GH5

Cel4A_Abi: Agaridus bisporus Cel4 (beta-mannanase). GeneBank Acc. #CAA90423
Man_Tre: Trichoderma reesei beta-mannanase. GeneBank Acc. #11514387

GH5_Ace     APAGFVTASGGQFVLNGLPYRYCGTNNYYLSYQ--SHA
Cel4a_Abi   VSTCFVKASGTRFTLNGQKYTVVGGNSYWVCLTGLSTS
Man_Tre     RASSFVTISGTQFNTDCKVCYFAGTNCYWCSFLT-NHA
            :.**. ** :* ::*      * * *:.    . :

GH5_Ace     DVDDVLAKAQAMNLSVIRTWGFIDIGSLDGSVPTIDGNKNGFYFQYWDPSTGAPAYNDGP
Cel4a_Abi   AMNQAFSDIANAGGTTVRTWGFNEVTSP-----------NGNYYQSWSGAR--PTTNTGA
Man_Tre     DVDSTFSHISSSCLKVVRVWGFNDVNTQPSP---------GQIWFQKLSATG--STINTGA
            :::..::.   . ...:*.*** :: :         .  ::* . :  .: * *.

GH5_Ace     TGLQGLDYAIASAAAHGLRVIVVLTNDWKEFGGMDQYD-KWYG-LPYHDNFYTDPRTQQA
Cel4a_Abi   SGLLNFDNVIAAAKANGIRLIVALTNNWADYGGMDVYVNQMVGNGQPHDLPYTNTAIKDA
Man_Tre     DGLQTLDYVVQSAEQHNLKLIIPFVNNWSDYGGINAYVNAFGG---NATTWYTNTAAQTQ
            **  :* .: :*   :.:::*:  :.*: :.*: :.* ::**::  *     *    :**:.  :

GH5_Ace     YKNWVNHLLNRVNSITGVTYKNDPTIFAWELANEPRCVGSGTLPTSGTCTQATIVNWVDQ
Cel4a_Abi   FKSYVRTFVSR--------YANEPTVMAWELANEPRCKGS-TGTTSGTCTTTTVTNWAKE
Man_Tre     YRKYVQAVVSR--------YANSTAIFAWELCNEPRCNGC---------STDVIVQWATS
            ::..:*.  .:..*       * *..:::****.***** *.          :  .:..:*. .

GH5_Ace     MSAYVKSIDPNHMVSVGDEGFYIGSTQGSGWPYNDPSDGVDNNALLRVKNIDFGTYHLYP
Cel4a_Abi   MSAFIKTIDSNHLVAIGDEGFYN-QPGAPTYPYQG-SEGVDFEANLAISSVDFATFHSYP
Man_Tre     VSQYVKSLDSNHLVTLGDEGLGLSTGDG-AYPYTY-GEGTDFAKNVQIKSLDFGTFHLYP
            :*  ::*::*.**:*::*****:       .   :**   ..:*.*     :  :..:**.:*  **

GH5_Ace     NYWOONAD---WGTQWIKDHIANAAAIGKPTILEEFGWQTPDRDSVYQTWTQTVRTNGEA
Cel4a_Abi   EPWGQGADAKAWGTQWITDHAASMKRVNKPVILEEFGVTTNQPD-TYAEWFNEVESSCLT
Man_Tre     DSWGTNYT---WGNGWIQTHAAACLAAGKPCVFEEYGAQQNPCTNEAPWQTTSLTTRGMG
            : ** .   **.**   * *   .**  .:*.*     :  :...:**.*:* **
```

Table 3-continued

Multiple amino acid sequence alignment of a ManA catalytic domain and polypeptides with Glycoside Hydrolase Family 5 catalytic domains.

```
GE5_Ace    GWNFWMLAGNVNGQPYPNYDGFNVYYPSSTATVLASEALAISTG
Ce14a_Abi  GDLIWQAGSHLSTGDTHN-DGYAVYPDGPVYPLMKSHASAMKNR
Man_Tre    GDMFWQWGDTFANGAQSNSDPYTVWYNSSNWQCLVKNHVDAING
           *  :*  .. .     * * : *:  ..   :  ..    .
```

Example 3

Mixed Domain GH5, CBD II, CBD III Genes and Hybrid Polypeptides

From the putative locations of the domains in the ManA sequence given above and in comparable cloned mannanase sequences from other species, one can separate individual domains and combine them with one or more domains from different sequences. The significant similarity between mannanase genes permit one by recombinant techniques to arrange one or more domains from the *Acidothermus cellulolyticus* ManA gene with one or more domains from a mannanase gene from one or more other microorganisms. Other representative endoglucanase genes include *Bacillus polymyxa* beta-(1,4) endoglucanase (Baird et al, Journal of Bacteriology, 172: 1576–86 (1992)) *Xanthomonas campestris* beta-(1,4)-endoglucanase (Gough et al, Gene 89:53–59 (1990)) and *Trichoderma harzianum* endo-1,3(4)-beta-glucanase (U.S. Pat. No. 6,140,096). The result of the fusion of any two or more domains will, upon expression, be a hybrid polypeptide. Such hybrid polypeptides can have one or more catalytic or binding domains. For ease of manipulation, recombinant techniques may be employed such as the addition of restriction enzyme sites by site-specific mutagenesis. If one is not using one domain of a particular gene, any number of any type of change including complete deletion may be made in the unused domain for convenience of manipulation.

It is understood for purposes of this disclosure, that various changes and modifications may be made to the invention that are well within the scope of the invention. Numerous other changes may be made which will readily suggest themselves to those skilled in the art and which are encompassed in the spirit of the invention disclosed herein and as defined in the appended claims.

This specification contains numerous citations to references such as patents, patent applications, and publications. Each is hereby incorporated by reference for all purposes.

What is claimed is:

1. A purified ManA polypeptide molecule capable of degrading mannose comprising:
   the sequence of SEQ ID NO:1.
2. A purified ManA polypeptide wherein its encoding nucleotide sequence in the same as SEQ ID NO: 2.
3. A composition comprising the polypeptide molecule of claim 1 and a carrier.
4. A method for reducing hemicellulose in a starting material, the method comprising:
   contacting the starting material with an effective amount of polypeptide molecule of claim 1.
5. An industrial detergent mixture suitable for degrading hemicellulose, said mixture comprising a purified ManA polypeptide having the sequence of SEQ ID NO. 1.
6. The industrial detergent mixture of claim 5, wherein said purified ManA polypeptide is further defined as having its encoding nucleotide sequence the same as SEQ ID NO:2.

* * * * *

SEQUENCE LISTING

```
<160> NUMBER OF SEQ ID NOS: 8

<210> SEQ ID NO 1
<211> LENGTH: 762
<212> TYPE: PRT
<213> ORGANISM: Acidothermus cellulolyticus

<400> SEQUENCE: 1

Met Gly Leu Val Arg Arg Pro Ala Arg Ala Phe Val Ala Thr Ala Ala
 1               5                  10                  15

Gly Thr Ala Val Ala Ala Ala Thr Leu Gly Ser Ile Thr Met Pro
             20                  25                  30

Ser Ala Thr Ala Ala Pro Ala Gly Phe Val Thr Ala Ser Gly Gly Gln
         35                  40                  45

Phe Val Leu Asn Gly Leu Pro Tyr Arg Tyr Gly Gly Thr Asn Asn Tyr
     50                  55                  60

Tyr Leu Ser Tyr Gln Ser His Ala Asp Val Asp Val Leu Ala Lys
 65                  70                  75                  80

Ala Gln Ala Met Asn Leu Ser Val Ile Arg Thr Trp Gly Phe Ile Asp
                 85                  90                  95

Ile Gly Ser Leu Asp Gly Ser Val Pro Thr Ile Asp Gly Asn Lys Asn
            100                 105                 110

Gly Phe Tyr Phe Gln Tyr Trp Asp Pro Ser Thr Gly Ala Pro Ala Tyr
        115                 120                 125

Asn Asp Gly Pro Thr Gly Leu Gln Gly Leu Asp Tyr Ala Ile Ala Ser
    130                 135                 140
```

-continued

| | | | | | | | | | | | | | | |
|---|---|---|---|---|---|---|---|---|---|---|---|---|---|---|
| Ala | Ala | Ala | His | Gly | Leu | Arg | Val | Ile | Val | Leu | Thr | Asn | Asp | Trp |
| 145 | | | | 150 | | | | 155 | | | | | | 160 |
| Lys | Glu | Phe | Gly | Gly | Met | Asp | Gln | Tyr | Asp | Lys | Trp | Tyr | Gly | Leu | Pro |
| | | | | 165 | | | | 170 | | | | | 175 | |
| Tyr | His | Asp | Asn | Phe | Tyr | Thr | Asp | Pro | Arg | Thr | Gln | Gln | Ala | Tyr | Lys |
| | | | 180 | | | | | 185 | | | | 190 | | | |
| Asn | Trp | Val | Asn | His | Leu | Leu | Asn | Arg | Val | Asn | Ser | Ile | Thr | Gly | Val |
| | | 195 | | | | | 200 | | | | | 205 | | | |
| Thr | Tyr | Lys | Asn | Asp | Pro | Thr | Ile | Phe | Ala | Trp | Glu | Leu | Ala | Asn | Glu |
| | 210 | | | | | 215 | | | | 220 | | | | | |
| Pro | Arg | Cys | Val | Gly | Ser | Gly | Thr | Leu | Pro | Thr | Ser | Gly | Thr | Cys | Thr |
| 225 | | | | | 230 | | | | | 235 | | | | | 240 |
| Gln | Ala | Thr | Ile | Val | Asn | Trp | Val | Asp | Gln | Met | Ser | Ala | Tyr | Val | Lys |
| | | | | 245 | | | | | 250 | | | | | 255 | |
| Ser | Ile | Asp | Pro | Asn | His | Met | Val | Ser | Val | Gly | Asp | Glu | Gly | Phe | Tyr |
| | | | 260 | | | | | 265 | | | | | 270 | | |
| Ile | Gly | Ser | Thr | Gln | Gly | Ser | Gly | Trp | Pro | Tyr | Asn | Asp | Pro | Ser | Asp |
| | | | 275 | | | | | 280 | | | | | 285 | | |
| Gly | Val | Asp | Asn | Asn | Ala | Leu | Leu | Arg | Val | Lys | Asn | Ile | Asp | Phe | Gly |
| | | 290 | | | | | 295 | | | | | 300 | | | |
| Thr | Tyr | His | Leu | Tyr | Pro | Asn | Tyr | Trp | Gly | Gln | Asn | Ala | Asp | Trp | Gly |
| 305 | | | | | 310 | | | | | 315 | | | | | 320 |
| Thr | Gln | Trp | Ile | Lys | Asp | His | Ile | Ala | Asn | Ala | Ala | Ile | Gly | Lys | |
| | | | | 325 | | | | | 330 | | | | | 335 | |
| Pro | Thr | Ile | Leu | Glu | Glu | Phe | Gly | Trp | Gln | Thr | Pro | Asp | Arg | Asp | Ser |
| | | | | 340 | | | | | 345 | | | | | 350 | |
| Val | Tyr | Gln | Thr | Trp | Thr | Gln | Thr | Val | Arg | Thr | Asn | Gly | Glu | Ala | Gly |
| | | | 355 | | | | | 360 | | | | | 365 | | |
| Trp | Asn | Phe | Trp | Met | Leu | Ala | Gly | Asn | Val | Asn | Gly | Gln | Pro | Tyr | Pro |
| | 370 | | | | | 375 | | | | | 380 | | | | |
| Asn | Tyr | Asp | Gly | Phe | Asn | Val | Tyr | Tyr | Pro | Ser | Ser | Thr | Ala | Thr | Val |
| 385 | | | | | 390 | | | | | 395 | | | | | 400 |
| Leu | Ala | Ser | Glu | Ala | Leu | Ala | Ile | Ser | Thr | Gly | Thr | Ser | Pro | Pro | Pro |
| | | | | 405 | | | | | 410 | | | | | 415 | |
| Ser | Pro | Ser | Ser | Ser | Pro | Ser | Ser | Pro | Ser | Pro | Ser | Pro | Ser | Pro | |
| | | | 420 | | | | | 425 | | | | | 430 | | |
| Ser | Ala | Ser | Pro | Ser | Ala | Ser | Pro | Ser | Ala | Ser | Ser | Pro | Ser | Pro | |
| | | 435 | | | | | 440 | | | | | 445 | | | |
| Ser | Pro | Ser | Ser | Ser | Pro | Val | Ser | Gly | Gly | Val | Lys | Val | Gln | Tyr | Lys |
| | 450 | | | | | 455 | | | | | 460 | | | | |
| Asn | Asn | Asp | Ser | Ala | Pro | Gly | Asp | Asn | Gln | Ile | Lys | Pro | Gly | Leu | Gln |
| 465 | | | | | 470 | | | | | 475 | | | | | 480 |
| Leu | Val | Asn | Thr | Gly | Ser | Ser | Ser | Val | Asp | Leu | Ser | Thr | Val | Thr | Val |
| | | | | 485 | | | | | 490 | | | | | 495 | |
| Arg | Tyr | Trp | Phe | Thr | Arg | Asp | Gly | Gly | Ser | Ser | Thr | Leu | Val | Tyr | Asn |
| | | | 500 | | | | | 505 | | | | | 510 | | |
| Cys | Asp | Trp | Ala | Ala | Met | Gly | Cys | Gly | Asn | Ile | Arg | Ala | Ser | Phe | Gly |
| | | | 515 | | | | | 520 | | | | | 525 | | |
| Ser | Val | Asn | Pro | Ala | Thr | Pro | Thr | Ala | Asp | Thr | Tyr | Leu | Gln | Leu | Ser |
| | | 530 | | | | | 535 | | | | | 540 | | | |
| Phe | Thr | Gly | Gly | Thr | Leu | Ala | Ala | Gly | Gly | Ser | Thr | Gly | Glu | Ile | Gln |
| 545 | | | | | 550 | | | | | 555 | | | | | 560 |
| Asn | Arg | Val | Asn | Lys | Ser | Asp | Trp | Ser | Asn | Phe | Asp | Glu | Thr | Asn | Asp |

-continued

```
                    565                 570                 575
Tyr Ser Tyr Gly Thr Asn Thr Ala Phe Gln Asp Trp Thr Lys Val Thr
                580                 585                 590

Val Tyr Val Asn Gly Arg Leu Val Trp Gly Thr Glu Pro Ser Gly Thr
            595                 600                 605

Ser Pro Ser Pro Thr Pro Ser Pro Ser Pro Thr Pro Ser Pro Ser Pro
        610                 615                 620

Ser Pro Thr Pro Ser Pro Ser Ser Pro Ser Pro Ser Pro Ser Pro
625                 630                 635                 640

Ser Pro Ser Pro Thr Pro Ser Pro Ser Pro Ser Pro Ser Pro
            645                 650                 655

Ser Val Ser Ser Ser Gly Val Gly Cys Arg Ala Thr Tyr Val Val Asn
                660                 665                 670

Ser Asp Trp Gly Ser Gly Phe Thr Ala Thr Val Thr Val Thr Asn Thr
            675                 680                 685

Gly Ser Arg Ala Thr Ser Gly Trp Thr Val Ala Trp Ser Phe Gly Gly
        690                 695                 700

Asn Gln Thr Val Thr Asn Tyr Trp Asn Thr Ala Leu Thr Gln Ser Gly
705                 710                 715                 720

Ala Ser Val Thr Ala Thr Asn Leu Ser Tyr Asn Asn Val Ile Gln Pro
            725                 730                 735

Gly Gln Ser Thr Thr Phe Gly Phe Asn Gly Ser Tyr Ser Gly Thr Asn
        740                 745                 750

Thr Ala Pro Thr Leu Thr Cys Thr Ala Ser
            755                 760

<210> SEQ ID NO 2
<211> LENGTH: 2289
<212> TYPE: DNA
<213> ORGANISM: Acidothermus cellulolyticus

<400> SEQUENCE: 2
atgggtctag tgcgtcgccc tgcgcgagca tttgttgcga ccgcggccgg cactgccgtt        60
gctgccgcgg cgacgctcgg ctcaatcacc atgccgtcag ccacgcagcc gccggcggga       120
ttcgtcaccg catccggcgg tcagttcgtt ctgaacggcc ttccctatcg ttacgggga       180 acgaacaact attacctcag ctatcagtcg cacgccgacg tcgatgacgt gttggccaag       240
gctcaagcga tgaatctttc tgtcatccgg acctggggtt tcatcgacat cggctctctt       300
gacggctccg tgcccacaat cgatggcaac aagaacggct tctactttca gtactgggac       360
ccgtcgaccg cgctccggc gtacaacgac gggccgaccg gcttgcaagg ccttgactac       420
gcgatcgcga gcgcggccgc gcacggcctt cgggtgattg tcgtcctcac caacgactgg       480
aaagaatttg ggggaatgga tcaatacgac aagtggtacg ccttccttac ccacgacaac       540
ttctacaccg accccggac ccagcaggcg tacaagaatt gggtcaatca tctactgaac       600
cgggtcaaca gcattaccgg cgtgacgtac aagaacgatc aacgatcttt gcttgggaa       660 cttgccaatg agccgcgctg cgtaggaagc ggcacattac aacctcgggg cacgtgcact       720
caggcgacca ttgtcaactg ggtcgatcaa atgtcggcgt acgtcaaaag catagaccct       780
aaccatatgg tctcggtcgg cgacgaaggg ttctacattg gtcaacgca gggaagcggc       840 tggccataca cgacccgtc cgacggcgtc gacaacaatg ctcttctccg tgtcaagaac       900
attgactttg gcacgtatca cctgtacccg aattactggg ccagaacgc ggactgggga       960 acgcaatgga tcaaggatca tattgcgaat gccgcagcga tcggcaagcc gaccattctc     1020
```

```
gaagaattcg gctggcagac accggaccgc gattccgtct atcagacgtg gacccagact      1080
gtgcgtacga acggtgaagc aggctggaac ttctggatgc tcgctgggaa tgtcaacggc      1140
cagccatatc cgaactatga cggcttcaac gtctactacc aagttcaac agcgaccgtc       1200 ctcgccagcg aggcgctcgc aatcagtacc ggcacatcgc ctccgccgtc gccgagctcg      1260
agtccatcct cgtcgccgtc tccgtcgccg tctccgtcgg cgtctccgtc ggcgtctccg      1320
tcggcgtctt cgtcgccgag cccgtctccg tcgtcgtcgc cggtgtcggg tggggtgaag      1380
gtgcagtaca agaacaatga ttcggcgccg ggtgataacc agatcaaacc gggtctccag      1440
ttggtgaata cggggtcgtc gtcggtggat ttgtcgacgg tgacggtgcg gtactggttc      1500
acccgggatg gtgggtcgtc gacactggtg tacaactgtg actgggcggc gatggggtgt     1560
gggaatatcc gcgcctcgtt cggctcggtg aaccggcga cgccgacggc ggacacctac       1620
ctgcagttgt cgttcactgg tggaacgttg gccgctggtg ggtcgacggg tgagattcaa      1680
aaccgggtga ataagagtga ctggtcgaac tttgatgaga ccaatgacta ctcgtatggg      1740
acgaacaccg ccttccagga ttggacgaag gtgacggtgt atgtcaatgg ccggctggtg      1800
tgggggactg aaccgtccgg caccagcccc agccccacac ccagccccag cccaaccccg      1860
tccccgagcc cgagcccgac ccaagcccc agctcctccc catccccgtc ccgagcccc       1920 agccccagcc ctacgccgtc cccgtcgccg agcccgtcgc cgtcgccgag tgtgtcgtcg      1980
tcgggtgtgg ggtgccggg gacgtatgtg gtgaatagtg attggggttc tgggtttacg      2040
gcgacggtga cggtgacgaa taccgggagc cgggcgacga gcgggtggac ggtggcgtgg      2100
tcgtttggtg ggaatcagac ggtcacgaac tactggaaca ctgcgttgac ccaatcaggt     2160
gcatcggtga cggcgacgaa cctgagctac aacaacgtga tccaaccggg tcagtcgacc      2220
accttcggat tcaacggaag ttactcagga caaacaccg cacctacact cacctgcacg      2280
gctagttga                                                              2289
```

<210> SEQ ID NO 3
<211> LENGTH: 375
<212> TYPE: PRT
<213> ORGANISM: Artificial Sequence
<220> FEATURE:
<223> OTHER INFORMATION: Description of Artificial Sequence: GH5 catalytic domain

<400> SEQUENCE: 3

```
Ala Pro Ala Gly Phe Val Thr Ala Ser Gly Gly Gln Phe Val Leu Asn
 1               5                  10                  15

Gly Leu Pro Tyr Arg Tyr Gly Gly Thr Asn Asn Tyr Tyr Leu Ser Tyr
            20                  25                  30

Gln Ser His Ala Asp Val Asp Val Leu Ala Lys Ala Gln Ala Met
        35                  40                  45

Asn Leu Ser Val Ile Arg Thr Trp Gly Phe Ile Asp Ile Gly Ser Leu
    50                  55                  60

Asp Gly Ser Val Pro Thr Ile Asp Gly Asn Lys Asn Gly Phe Tyr Phe
65                  70                  75                  80

Gln Tyr Trp Asp Pro Ser Thr Gly Ala Pro Tyr Asn Asp Gly Pro
                85                  90                  95

Thr Gly Leu Gln Gly Leu Asp Tyr Ala Ile Ala Ser Ala Ala Ala His
            100                 105                 110

Gly Leu Arg Val Ile Val Val Leu Thr Asn Asp Trp Lys Glu Phe Gly
        115                 120                 125
```

-continued

```
Gly Met Asp Gln Tyr Asp Lys Trp Tyr Gly Leu Pro Tyr His Asp Asn
            130                 135                 140

Phe Tyr Thr Asp Pro Arg Thr Gln Gln Ala Tyr Lys Asn Trp Val Asn
145                 150                 155                 160

His Leu Leu Asn Arg Val Asn Ser Ile Thr Gly Val Thr Tyr Lys Asn
                165                 170                 175

Asp Pro Thr Ile Phe Ala Trp Glu Leu Ala Asn Glu Pro Arg Cys Val
            180                 185                 190

Gly Ser Gly Thr Leu Pro Thr Ser Gly Thr Cys Thr Gln Ala Thr Ile
        195                 200                 205

Val Asn Trp Val Asp Gln Met Ser Ala Tyr Val Lys Ser Ile Asp Pro
    210                 215                 220

Asn His Met Val Ser Val Gly Asp Glu Gly Phe Tyr Ile Gly Ser Thr
225                 230                 235                 240

Gln Gly Ser Gly Trp Pro Tyr Asn Asp Pro Ser Asp Gly Val Asp Asn
                245                 250                 255

Asn Ala Leu Leu Arg Val Lys Asn Ile Asp Phe Gly Thr Tyr His Leu
            260                 265                 270

Tyr Pro Asn Tyr Trp Gly Gln Asn Ala Asp Trp Gly Thr Gln Trp Ile
        275                 280                 285

Lys Asp His Ile Ala Asn Ala Ala Ile Gly Lys Pro Thr Ile Leu
    290                 295                 300

Glu Glu Phe Gly Trp Gln Thr Pro Asp Arg Asp Ser Val Tyr Gln Thr
305                 310                 315                 320

Trp Thr Gln Thr Val Arg Thr Asn Gly Glu Ala Gly Trp Asn Phe Trp
                325                 330                 335

Met Leu Ala Gly Asn Val Asn Gly Gln Pro Tyr Pro Asn Tyr Asp Gly
            340                 345                 350

Phe Asn Val Tyr Tyr Pro Ser Ser Thr Ala Thr Val Leu Ala Ser Glu
        355                 360                 365

Ala Leu Ala Ile Ser Thr Gly
    370                 375

<210> SEQ ID NO 4
<211> LENGTH: 154
<212> TYPE: PRT
<213> ORGANISM: Artificial Sequence
<220> FEATURE:
<223> OTHER INFORMATION: Description of Artificial Sequence:
      Carbohydrate binding domain

<400> SEQUENCE: 4

Val Ser Gly Gly Val Lys Val Gln Tyr Lys Asn Asn Asp Ser Ala Pro
1               5                   10                  15

Gly Asp Asn Gln Ile Lys Pro Gly Leu Gln Leu Val Asn Thr Gly Ser
            20                  25                  30

Ser Ser Val Asp Leu Ser Thr Val Thr Val Arg Tyr Trp Phe Thr Arg
        35                  40                  45

Asp Gly Gly Ser Ser Thr Leu Val Tyr Asn Cys Asp Trp Ala Ala Met
    50                  55                  60

Gly Cys Gly Asn Ile Arg Ala Ser Phe Gly Ser Val Asn Pro Ala Thr
65                  70                  75                  80

Pro Thr Ala Asp Thr Tyr Leu Gln Leu Ser Phe Thr Gly Gly Thr Leu
                85                  90                  95

Ala Ala Gly Gly Ser Thr Gly Glu Ile Gln Asn Arg Val Asn Lys Ser
```

```
                     100                 105                 110
Asp Trp Ser Asn Phe Asp Glu Thr Asn Asp Tyr Ser Tyr Gly Thr Asn
            115                 120                 125

Thr Ala Phe Gln Asp Trp Thr Lys Val Thr Val Tyr Val Asn Gly Arg
    130                 135                 140

Leu Val Trp Gly Thr Glu Pro Ser Gly Thr
145                 150

<210> SEQ ID NO 5
<211> LENGTH: 101
<212> TYPE: PRT
<213> ORGANISM: Artificial Sequence
<220> FEATURE:
<223> OTHER INFORMATION: Description of Artificial Sequence:
      Carbohydrate binding domain

<400> SEQUENCE: 5

Gly Val Gly Cys Arg Ala Thr Tyr Val Val Asn Ser Asp Trp Gly Ser
1               5                   10                  15

Gly Phe Thr Ala Thr Val Thr Val Thr Asn Thr Gly Ser Arg Ala Thr
            20                  25                  30

Ser Gly Trp Thr Val Ala Trp Ser Phe Gly Gly Asn Gln Thr Val Thr
        35                  40                  45

Asn Tyr Trp Asn Thr Ala Leu Thr Gln Ser Gly Ala Ser Val Thr Ala
    50                  55                  60

Thr Asn Leu Ser Tyr Asn Asn Val Ile Gln Pro Gly Gln Ser Thr Thr
65                  70                  75                  80

Phe Gly Phe Asn Gly Ser Tyr Ser Gly Thr Asn Thr Ala Pro Thr Leu
                85                  90                  95

Thr Cys Thr Ala Ser
            100

<210> SEQ ID NO 6
<211> LENGTH: 375
<212> TYPE: PRT
<213> ORGANISM: Acidothermus cellulolyticus

<400> SEQUENCE: 6

Ala Pro Ala Gly Phe Val Thr Ala Ser Gly Gln Phe Val Leu Asn
1               5                   10                  15

Gly Leu Pro Tyr Arg Tyr Gly Gly Thr Asn Asn Tyr Tyr Leu Ser Tyr
            20                  25                  30

Gln Ser His Ala Asp Val Asp Val Leu Ala Lys Ala Gln Ala Met
        35                  40                  45

Asn Leu Ser Val Ile Arg Thr Trp Gly Phe Ile Asp Ile Gly Ser Leu
    50                  55                  60

Asp Gly Ser Val Pro Thr Ile Asp Gly Asn Lys Asn Gly Phe Tyr Phe
65                  70                  75                  80

Gln Tyr Trp Asp Pro Ser Thr Gly Ala Pro Ala Tyr Asn Asp Gly Pro
                85                  90                  95

Thr Gly Leu Gln Gly Leu Asp Tyr Ala Ile Ala Ser Ala Ala Ala His
            100                 105                 110

Gly Leu Arg Val Ile Val Leu Thr Asn Asp Trp Lys Glu Phe Gly
        115                 120                 125

Gly Met Asp Gln Tyr Asp Lys Trp Tyr Gly Leu Pro Tyr His Asp Asn
    130                 135                 140

Phe Tyr Thr Asp Pro Arg Thr Gln Gln Ala Tyr Lys Asn Trp Val Asn
```

```
145                 150                 155                 160
His Leu Leu Asn Arg Val Asn Ser Ile Thr Gly Val Thr Tyr Lys Asn
                165                 170                 175

Asp Pro Thr Ile Phe Ala Trp Glu Leu Ala Asn Glu Pro Arg Cys Val
            180                 185                 190

Gly Ser Gly Thr Leu Pro Thr Ser Gly Thr Cys Thr Gln Ala Thr Ile
        195                 200                 205

Val Asn Trp Val Asp Gln Met Ser Ala Tyr Val Lys Ser Ile Asp Pro
    210                 215                 220

Asn His Met Val Ser Val Gly Asp Glu Gly Phe Tyr Ile Gly Ser Thr
225                 230                 235                 240

Gln Gly Ser Gly Trp Pro Tyr Asn Asp Pro Ser Asp Gly Val Asp Asn
                245                 250                 255

Asn Ala Leu Leu Arg Val Lys Asn Ile Asp Phe Gly Thr Tyr His Leu
            260                 265                 270

Tyr Pro Asn Tyr Trp Gly Gln Asn Ala Asp Trp Gly Thr Gln Trp Ile
        275                 280                 285

Lys Asp His Ile Ala Asn Ala Ala Ala Ile Gly Lys Pro Thr Ile Leu
    290                 295                 300

Glu Glu Phe Gly Trp Gln Thr Pro Asp Arg Asp Ser Val Tyr Gln Thr
305                 310                 315                 320

Trp Thr Gln Thr Val Arg Thr Asn Gly Glu Ala Gly Trp Asn Phe Trp
                325                 330                 335

Met Leu Ala Gly Asn Val Asn Gly Gln Pro Tyr Pro Asn Tyr Asp Gly
            340                 345                 350

Phe Asn Val Tyr Tyr Pro Ser Ser Thr Ala Thr Val Leu Ala Ser Glu
        355                 360                 365

Ala Leu Ala Ile Ser Thr Gly
370                 375

<210> SEQ ID NO 7
<211> LENGTH: 356
<212> TYPE: PRT
<213> ORGANISM: Agaricus bisporus

<400> SEQUENCE: 7

Val Ser Thr Gly Phe Val Lys Ala Ser Gly Thr Arg Phe Thr Leu Asn
 1               5                  10                  15

Gly Gln Lys Tyr Thr Val Gly Gly Asn Ser Tyr Trp Val Gly Leu
                20                  25                  30

Thr Gly Leu Ser Thr Ser Ala Met Asn Gln Ala Phe Ser Asp Ile Ala
            35                  40                  45

Asn Ala Gly Gly Thr Thr Val Arg Thr Trp Gly Phe Asn Glu Val Thr
        50                  55                  60

Ser Pro Asn Gly Asn Tyr Tyr Gln Ser Trp Ser Gly Ala Arg Pro Thr
65                  70                  75                  80

Ile Asn Thr Gly Ala Ser Gly Leu Leu Asn Phe Asp Asn Val Ile Ala
                85                  90                  95

Ala Ala Lys Ala Asn Gly Ile Arg Leu Ile Val Ala Leu Thr Asn Asn
            100                 105                 110

Trp Ala Asp Tyr Gly Gly Met Asp Val Tyr Val Asn Gln Met Val Gly
        115                 120                 125

Asn Gly Gln Pro His Asp Leu Phe Tyr Thr Asn Thr Ala Ile Lys Asp
    130                 135                 140
```

```
Ala Phe Lys Ser Tyr Val Arg Thr Phe Val Ser Arg Tyr Ala Asn Glu
145                 150                 155                 160

Pro Thr Val Met Ala Trp Glu Leu Ala Asn Glu Pro Arg Cys Lys Gly
            165                 170                 175

Ser Thr Gly Thr Thr Ser Gly Thr Cys Thr Thr Thr Val Thr Asn
        180                 185                 190

Trp Ala Lys Glu Met Ser Ala Phe Ile Lys Thr Ile Asp Ser Asn His
        195                 200                 205

Leu Val Ala Ile Gly Asp Glu Gly Phe Tyr Asn Gln Pro Gly Ala Pro
    210                 215                 220

Thr Tyr Pro Tyr Gln Gly Ser Glu Gly Val Asp Phe Glu Ala Asn Leu
225                 230                 235                 240

Ala Ile Ser Ser Val Asp Phe Ala Thr Phe His Ser Tyr Pro Glu Pro
                245                 250                 255

Trp Gly Gln Gly Ala Asp Ala Lys Ala Trp Gly Thr Gln Trp Ile Thr
            260                 265                 270

Asp His Ala Ala Ser Met Lys Arg Val Asn Lys Pro Val Ile Leu Glu
        275                 280                 285

Glu Phe Gly Val Thr Thr Asn Gln Pro Asp Thr Tyr Ala Glu Trp Phe
    290                 295                 300

Asn Glu Val Glu Ser Ser Gly Leu Thr Gly Asp Leu Ile Trp Gln Ala
305                 310                 315                 320

Gly Ser His Leu Ser Thr Gly Asp Thr His Asn Asp Gly Tyr Ala Val
                325                 330                 335

Tyr Pro Asp Gly Pro Val Tyr Pro Leu Met Lys Ser His Ala Ser Ala
            340                 345                 350

Met Lys Asn Arg
        355

<210> SEQ ID NO 8
<211> LENGTH: 346
<212> TYPE: PRT
<213> ORGANISM: Trichoderma reesei

<400> SEQUENCE: 8

Arg Ala Ser Ser Phe Val Thr Ile Ser Gly Thr Gln Phe Asn Ile Asp
1               5                   10                  15

Gly Lys Val Gly Tyr Phe Ala Gly Thr Asn Cys Tyr Trp Cys Ser Phe
            20                  25                  30

Leu Thr Asn His Ala Asp Val Asp Ser Thr Phe Ser His Ile Ser Ser
        35                  40                  45

Ser Gly Leu Lys Val Val Arg Val Trp Gly Phe Asn Asp Val Asn Thr
    50                  55                  60

Gln Pro Ser Pro Gly Gln Ile Trp Phe Gln Lys Leu Ser Ala Thr Gly
65                  70                  75                  80

Ser Thr Ile Asn Thr Gly Ala Asp Gly Leu Gln Thr Leu Asp Tyr Val
                85                  90                  95

Val Gln Ser Ala Glu Gln His Asn Leu Lys Leu Ile Ile Pro Phe Val
            100                 105                 110

Asn Asn Trp Ser Asp Tyr Gly Gly Ile Asn Ala Tyr Val Asn Ala Phe
        115                 120                 125

Gly Gly Asn Ala Thr Thr Trp Tyr Thr Asn Thr Ala Ala Gln Thr Gln
    130                 135                 140

Tyr Arg Lys Tyr Val Gln Ala Val Val Ser Arg Tyr Ala Asn Ser Thr
145                 150                 155                 160
```

```
Ala Ile Phe Ala Trp Glu Leu Gly Asn Glu Pro Arg Cys Asn Gly Cys
            165                 170                 175

Ser Thr Asp Val Ile Val Gln Trp Ala Thr Ser Val Ser Gln Tyr Val
            180                 185                 190

Lys Ser Leu Asp Ser Asn His Leu Val Thr Leu Gly Asp Glu Gly Leu
        195                 200                 205

Gly Leu Ser Thr Gly Asp Gly Ala Tyr Pro Tyr Thr Tyr Gly Glu Gly
        210                 215                 220

Thr Asp Phe Ala Lys Asn Val Gln Ile Lys Ser Leu Asp Phe Gly Thr
225                 230                 235                 240

Phe His Leu Tyr Pro Asp Ser Trp Gly Thr Asn Tyr Thr Trp Gly Asn
            245                 250                 255

Gly Trp Ile Gln Thr His Ala Ala Ala Cys Leu Ala Ala Gly Lys Pro
            260                 265                 270

Cys Val Phe Glu Glu Tyr Gly Ala Gln Gln Asn Pro Cys Thr Asn Glu
            275                 280                 285

Ala Pro Trp Gln Thr Thr Ser Leu Thr Thr Arg Gly Met Gly Gly Asp
    290                 295                 300

Met Phe Trp Gln Trp Gly Asp Thr Phe Ala Asn Gly Ala Gln Ser Asn
305                 310                 315                 320

Ser Asp Pro Tyr Thr Val Trp Tyr Asn Ser Ser Asn Trp Gln Cys Leu
            325                 330                 335

Val Lys Asn His Val Asp Ala Ile Asn Gly
            340                 345
```